(12) United States Patent
Ota et al.

(10) Patent No.: US 6,472,397 B1
(45) Date of Patent: Oct. 29, 2002

(54) NITROGEN-CONTAINING HETEROCYCLIC COMPOUNDS HAVING ANTIPLATELET AGGREGATION EFFECT AND MEDICINAL USE THEREOF

(75) Inventors: Kazumi Ota, Yokohama (JP); Kazuko Kobayashi, Yokohama (JP); Tomoaki Miura, Yokohama (JP); Takahiro Imai, Yokohama (JP); Kazumasa Aizawa, Yokohama (JP); Hisashi Suzuki, Yokohama (JP); Shokichi Ohuchi, Yokohama (JP); Kiyoaki Katano, Yokohama (JP); Takashi Ando, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 09/647,849

(22) PCT Filed: Jun. 16, 1998

(86) PCT No.: PCT/JP98/02641

§ 371 (c)(1),
(2), (4) Date: Nov. 3, 2000

(87) PCT Pub. No.: WO99/52894

PCT Pub. Date: Oct. 21, 1999

(30) Foreign Application Priority Data

Apr. 9, 1998 (JP) ............................. 10-097051

(51) Int. Cl.⁷ ..................... A61K 31/44; A61K 31/445; C07D 241/04; C07D 295/00; C07D 401/00
(52) U.S. Cl. ............................ 514/253.01; 514/253.13; 514/326; 514/330; 514/331; 514/341; 544/384; 544/360; 544/386; 544/399; 544/402; 544/403; 546/189; 546/210; 546/229; 546/237; 546/329; 546/339
(58) Field of Search ................ 514/253.13, 253.01, 514/326, 330, 331, 341; 544/360, 384, 386, 399, 402, 403; 546/189, 210, 229, 237, 329, 339

(56) References Cited

FOREIGN PATENT DOCUMENTS

| DE | 44 46 301 | 4/1996 |
|---|---|---|
| WO | 96/02503 | 2/1996 |
| WO | 9602503 | * 2/1996 |
| WO | 96/20173 | 7/1996 |
| WO | 98/00134 | 1/1998 |

* cited by examiner

Primary Examiner—Richard L. Raymond
Assistant Examiner—Sudhaker B. Patel
(74) Attorney, Agent, or Firm—Wenderoth, Lind & Ponack, L.L.P.

(57) ABSTRACT

The compounds represented by the formula (I), and pharmacologically acceptable salts and solvates thereof are disclosed. The compound is hydrolyzed in organisms into a compound represented by the formula in which W represents a hydrogen atom, and D represents the group —V—$(CH_2)_p$—COOR, wherein R represents a hydrogen atom. The compound inhibits the aggregation of platelets via the inhibition of the linkage of the platelet membrane protein GPIIb/IIIa to fibrinogen.

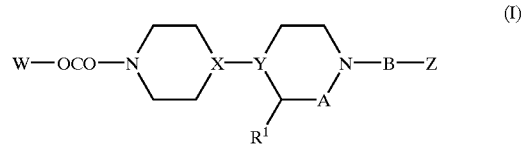

(I)

wherein A represents $CH_2$ or CO, B represents the group —$(CH_2)_k$— or —$(CH_2)_m$—CO—, X and Y are different from each other and represent N or CH, W represents an ester moiety which can be removed under the physiological condition, and Z represents the groups (II) or (III):

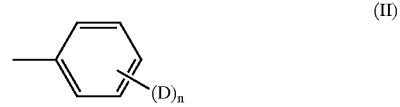

(II)

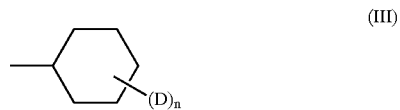

(III)

wherein D represents the group —V—$(CH_2)_p$—COOR.

19 Claims, No Drawings

NITROGEN-CONTAINING HETEROCYCLIC COMPOUNDS HAVING ANTIPLATELET AGGREGATION EFFECT AND MEDICINAL USE THEREOF

This application is a 371 of PCT/JP98/02641 filed Jun. 16, 1998.

BACKGROUND OF THE INVENTION

1. Field of the Invention

The present invention relates to nitrogen-containing heterocyclic compounds which inhibit the aggregation of platelets, and pharmaceutical compositions comprising the compound as an effective ingredient, which are effective for the treatment and prophylaxis of thrombotic diseases.

2. Background Art

Diseases in the cardiovascular system have increased with the change of diet or the increase of the aged population, and about 50% of these diseases is regarded to be caused by thrombus.

Platelet as an ingredient of plasma participates largely in the production of thrombus in body. For the treatment and prophylaxis of thrombotic diseases, there have thus been used clinically pharmaceuticals which suppress the function of platelets and inhibit the aggregation of platelets, for example aspirin which suppresses cyclooxygenase and cyclopyridine which activates adenylcyclase.

Recently, the analysis of glycoproteins has been progressively analyzed. It has been elucidated that a membrane glycoprotein referred to as GPIIb/IIIa has a function as a receptor of fibrinogen. Thus, an antagonist of the membrane glycoprotein GPIIb/IIIa has been expected to be effective for the treatment and prophylaxis of the thrombotic diseases as a platelet aggregation inhibitor having a new reaction mechanism (Trends in Pharmacological Science, 13, 413, 1992). There has been known as the compounds having such antagonistic effects monoclonal antibody (Ann. New York Acad. Sci., 614, 193, 1991), tripeptide derivatives comprising arginine-glycine-aspartic acid (J. Med. Chem., 35, 2040, 1992), amidinophenyl derivatives (J. Med. Chem., 35, 4393, 1992; Japanese Patent Laid-Open Publication No.4-264068, Japanese Patent Laid-Open Publication No. 4-334351, EP 483667, EP 525629, EP 529858, EP 537980, WO 9307867, WO 9402472, and the like), tyrosine derivatives (J. Med. Chem., 35, 4640, 1992), piperidine derivatives (EP 512831, EP 540334, EP 578535, and the like).

On the other hand, there have been desired as therapeutic and prophylactic agents of thrombotic diseases a highly selective agent having no side effects such as hemorrhage and a highly active antagonist effective even on its oral administration.

SUMMARY OF THE INVENTION

The present inventors have now prepared novel nitrogen-containing heterocyclic compounds having extremely high oral absorbing capacity.

The compounds according to the present invention are the compounds represented by the following general formula (I), and pharmaceutically acceptable salts and solvates thereof.

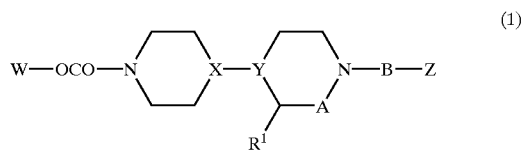

wherein
A represents $CH_2$ or CO,
B represents a group —$(CH_2)_k$—, where k is an integer of 1–4, or —$(CH_2)_m$—CO—, where m is an integer of 0–3,
X and Y, which are different from each other, represent N or CH,
W represents an ester moiety which can be removed under the physiological condition,
Z represents the group (II) or (III)

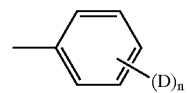

wherein
n is an integer of 1–3,
D represents the group —V—$(CH_2)_p$—COOR, where V represents —O— or a bond, p is an integer of 1–4, R represents a hydrogen atom, $C_{1-8}$ alkyl, which may be substituted by a halogen atom, $C_{3-8}$ cycloalkyl, benzyl, five- to eight-membered saturated cycloalkyl containing an oxygen or sulfur atom, 1,3-bis($C_{1-6}$alkoxy)propan-2-yl, 1,3-bis($C_{1-6}$alkylthio)propan-2-yl, $C_{1-6}$alkyl-$(OCH_2CH_2)_q$— where q is an integer of 1–3, $C_{1-6}$alkyl-$(SCH_2CH_2)_r$— where r is an integer of 1–3, R'R''NCO—$(CH_2)_s$— where s is an integer of 1–3, and R' and R'' independently represent a hydrogen atom or $C_{1-6}$alkyl, or an ester moiety which may be removed under a physiological condition,
$R^1$ represents a hydrogen atom or $C_{1-6}$ alkyl which may be substituted by carboxyl, lower alkoxyl, carbamoyl, or phenyl.

SPECIFIC DESCRIPTION OF THE INVENTION

Definition

In the present specification, alkyl, alkenyl and alkynyl groups may be either of straight chain or branched chain. The term "halogen atom" means herein fluorine, chlorine, bromine or iodine atoms. The term "aryl" means preferably phenyl, naphthyl or tolyl. Furthermore, the term "aralkyl" means preferably benzyl, phenylethyl (phenethyl), or methylbenzyl.

Compounds of the Formula (I)

In the formula (I), A represents $CH_2$ or CO. According to the preferred embodiment of the present invention, the compound of the formula (I) wherein A represents CO is preferred.

In the formula (I), B represents the group —$(CH_2)_k$—, wherein k is an integer of 1–4, preferably 1 or 2, or the group —$(CH_2)_m$—CO—, wherein m is an integer of 0–3, preferably 0, 1 or 2. According to the preferred embodiment of the present invention, B preferably represents the group —$(CH_2)_m$—CO—, more preferably the group —$CH_2$—CO—.

In the formula (I), X and Y are different from each other and represent N or CH. According to the preferred embodiment of the present invention, X represents CH and Y represents N.

In the formula (I), W represents an ester moiety which can be removed under a physiological condition. The first example of the preferred ester moiety is the following group represented by the formula (a):

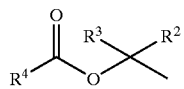

(a)

wherein $R^2$ and $R^3$ represent independently a hydrogen atom or $C_{1-6}$ alkyl (preferably $C_{1-4}$ alkyl), $R^4$ represents $C_{1-10}$ alkyl (preferably $C_{1-6}$ alkyl, more preferably $C_{1-4}$ alkyl), $C_{2-10}$ alkenyl (preferably $C_{2-6}$ alkenyl, more preferably $C_{2-4}$ alkenyl), $C_{2-5}$ alkynyl, aryl such as phenyl, naphthyl or tolyl, or $C_{3-8}$ cycloalkyl (preferably $C_{5-8}$ cycloalkyl). According to the preferred embodiment of the present invention, the compounds of the formula (I) having the group (a) where $R^2$ represents a hydrogen atom, $R^3$ represents a hydrogen atom or $C_{1-6}$ alkyl, and $R^4$ represents $C_{1-6}$ alkyl are preferred.

The second example of the preferred ester moiety is the following group represented by the formula (b):

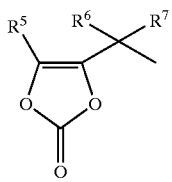

(b)

wherein $R^5$ represents a hydrogen atom, $C_{1-6}$ alkyl (preferably $C_{1-4}$ alkyl), or $C_{6-8}$ aralkyl such as benzyl, phenylethyl (phenethyl) or methylbenzyl, $R^6$ and $R^7$ independently represent a hydrogen atom or $C_{1-6}$ alkyl (preferably $C_{1-4}$ alkyl). According to the preferred embodiment of the present invention, the compounds of the formula (I) having the group (b) where $R^5$ represents $C_{1-6}$ alkyl, and $R^6$ and $R^7$ represent a hydrogen atom are preferred.

The third example of the preferred ester moiety is the following group represented by the formula (c):

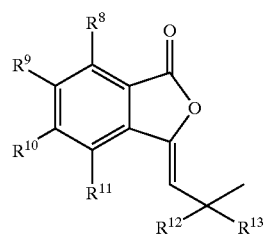

(c)

wherein $R^8$, $R^9$, $R^{10}$ and $R^{11}$ independently represent a hydrogen atom, $C_{1-6}$ alkyl or $C_{6-8}$ aralkyl, $R^{12}$ and $R^{13}$ independently represent a hydrogen atom or $C_{1-6}$ alkyl. According to the preferred embodiment of the present invention,in the group (c), $R^8$, $R^9$, $R^{10}$ and $R^{11}$ represent a hydrogen atom, $R^{12}$ and $R^{13}$ represent a hydrogen atom.

In the formula (I), Z represents the groups represented by the formula (II) or (III). In the groups (II) and (III), n is an integer of 1–3, preferably 1 or 2. This means that the number of the substituent D is 1–3, preferably 1 or 2. In addition, the substituent D is at the para or meta position to that of the substituent B.

In the group —V—$(CH_2)_p$—COOR in the group Z, V represents an oxygen atom or a bond. According to the preferred embodiment of the present invention, V is an oxygen atom. In the group, p is an integer of 1–4, preferably 1 or 2. In addition, R represents a hydrogen atom, $C_{1-8}$ alkyl which may be substituted by a halogen atom, $C_{3-8}$ cycloalkyl, benzyl, a five- to eight-membered saturated cycloalkyl group containing an oxygen or sulfur atom, preferably a five- to eight-membered saturated cycloalkyl group containing an oxygen atom, more preferably tetrahydropyranyl, 1,3-bis($C_{1-6}$ alkoxy)propan-2-yl, (preferably 1,3-bis($C_{1-4}$ alkoxy)propan-2-yl), 1,3-bis($C_{1-6}$ alkylthio)propan-2-yl (preferably 1,3-bis-($C_{1-4}$ alkylthio) propan-2-yl), $C_{1-6}$ alkyl-$(OCH_2CH_2)_q$—, wherein q is an integer of 1–3, $C_{1-6}$ alkyl-$(SCH_2CH_2)_r$— wherein r is an integer of 1–3, R'R"NCO—$(CH_2)_s$—, wherein s is an integer of 1–3, and R' and R" independently represent a hydrogen atom or $C_{1-6}$ alkyl (preferably $C_{1-4}$ alkyl), or an ester moiety which can be removed under a physiological condition such as pivaloyloxymethyl, 1-(cyclohexyloxy-carbonyloxy)ethyl or (5-methyl-2-oxo-1,3-dioxol-4-yl) methyl.

According to the preferred embodiment of the present invention, Z represents the group (II) where R represents $C_{1-8}$ alkyl which may be substituted by halogen atoms, $C_{5-8}$ cycloalkyl, benzyl, a five- to eight-membered saturated cycloalkyl group containing an oxygen or sulfur atom, 1,3-bis($C_{1-6}$ alkoxy)propan-2-yl, or a R'R"NCO—$(CH_2)_s$—, wherein s is 1, and R' and R" independently represent a hydrogen atom or $C_{1-6}$ alkyl, respectively.

In the formula (I), $R^1$ represents a hydrogen atom or $C_{1-6}$ alkyl (preferably $C_{1-4}$ alkyl), which may be substituted by carboxyl, $C_{1-6}$ alkoxy, carbamoyl or phenyl.

A preferred class of the compounds of the present invention include the compounds wherein Z represents the group (II) where R represents $C_{1-8}$ alkyl which may be substituted by halogen atoms, $C_{5-8}$ cycloalkyl, benzyl, a five- to eight-membered saturated cycloalkyl group containing an oxygen or sulfur atom, 1,3-bis($C_{1-6}$ alkoxy)propan-2-yl, or R'R"NCO —$(CH_2)_s$—, wherein s is 1, and R' and R" independently represent a hydrogen atom or $C_{1-6}$ alkyl, respectively, and among these compounds are more preferably those wherein W represents the group (a) where $R^2$ represents a hydrogen atom, $R^3$ represents a hydrogen atom or $C_{1-6}$ alkyl, and $R^4$ represents $C_{1-6}$ alkyl, W represents the group (b) where $R^5$ represents $C_{1-6}$ alkyl, and $R^6$ and $R^7$ represent a hydrogen atom, W represents the group (c) where $R^8$, $R^9$, $R^{10}$ and $R^{11}$ represent a hydrogen atom, and $R^{12}$ and $R^{13}$ represent a hydrogen atom.

According to another preferred embodiment of the present invention, another preferred class of the compounds group of the present invention includes the compounds represented by the formula (I) wherein A represents CO, $R^1$ represents a hydrogen atom, X represents CH, and Y represents N, and the more preferred compound group includes the compounds wherein A represents CO, $R^1$ represents a hydrogen atom, X represents CH, Y represents N, and B represents —$(CH_2)_m$—CO—.

The preferred examples of the compounds according to the present invention include ethyl 4-[[2-oxo-4-(1-pivaloyloxymethoxycarbonylpiperidin-4-yl)piperazin-1-yl]acetyl]phenoxyacetate, isopropyl 4-[[2-oxo-4-(1-pivaloyloxymethoxycarbonylpiperidin-4-yl)piperazin-1-yl]acetyl]phenoxyacetate, ethyl 4-[[2-oxo-4-[1-(1-pivaloyloxyethyl)oxycarbonylpiperidin-4-yl]piperazin-1-yl]acetyl]phenoxyacetate, ethyl 4-[[2-oxo-4-[1-(1-pivaloyloxy-2-methylpropyl)oxycarbonylpiperidin-4-yl ]piperazin-1-yl]acetyl]phenoxyacetate, ethyl 4-[[4-(1-acetoxymethoxycarbonylpiperidin-4-yl)-2-oxopiperazin-1-yl]acetyl]phenoxyacetate, isopropyl 4-[[4-(1-acetoxymethoxycarbonylpiperidin-4-yl)-2-oxopiperazin-1-yl]acetyl]phenoxyacetate, cyclohexyl 4-[[4-(1-acetoxymethoxycarbonylpiperidin-4-yl)-2-oxopiperazin-1-yl]acetyl]phenoxyacetate, ethyl 4-[[4-[1-(1-acetoxyethyl)oxycarbonylpiperidin-4-yl]-2-oxopiperazin-1-yl]acetyl]phenoxyacetate, cyclohexyl 4-[[4-[1-(1-acetoxyethyl)oxycarbonylpiperidin-4-yl]-2-oxopiperazin-1-yl]acetyl]phenoxyacetate, methyl 4-[[4-[1-(1-acetoxyetyl)oxycarbonylpiperidin-4-yl]-2-oxopiperazin-1-yl]acetyl]phenoxyacetate, ethyl 4-[[4-[1-(1-acetoxypropyl)oxycarbonylpiperidin-4-yl]-2-oxopiperazin-1-yl]acetyl]phenoxyacetate, cyclohexyl 4-[[4-[1-(1-acetoxy-2-methylpropyl)oxycarbonylpiperidin-4-yl]-2-oxopiperazin-1-yl]acetyl]phenoxyacetate, ethyl 4-[[4-[1-acetoxy-2-methylpropyl]oxycarbonylpiperidin-4-yl]-2-oxopiperazin-1-yl]acetyl]phenoxyacetate, isopropyl 4-[[4-[1-(1-acetoxy-2-methylpropyl)oxycarbonylpiperidin-4-yl]-2-oxopiperazin-1-yl]acetyl]phenoxyacetate, ethyl 4-[[4-[1-(1-acetoxy-2,2-dimethylpropyl)oxycarbonylpiperidin-4-yl]-2-oxopiperazin-1-yl]acetyl]phenoxyacetate, ethyl 4-[[2-oxo-4-[1-(1-propionyloxyethyl)oxycarbonylpiperidin-4-yl]piperazin-1-yl]acetyl]phenoxyacetate, ethyl 4-[[2-oxo-4-[1-(propionyloxy-2-methylpropyl)oxycarbonylpiperidin-4-yl]piperazin-1-yl]acetyl]phenoxyacetate, n-butyl 4-[[4-[(5-methyl-2-oxo-1,3-dioxol-4-yl)methyl oxycarbonylpiperidin-4-yl]-2-oxopiperazin-1-yl]acetyl]phenoxyacetate, and ethyl 4-[[2-oxo-4-[(Z)-2-(3-phthalidyliden)ethyloxycarbonylpiperidin-4-yl)piperazin-1-yl]acetyl]phenoxyacetate.

The more preferred compounds include ethyl 4-[2-oxo-4-(1-pivaloyloxymethoxycarbonylpiperidin-4-yl)piperazin-1-yl]acetyl]phenoxyacetate, isopropyl 4-[[2-oxo-4-(1-pivaloyloxymethoxycarbonylpiperidin-4-yl)piperazin-1-yl]acetyl]phenoxyacetate, and ethyl 4-[[4-(1-acetoxymethoxycarbonylpiperidin-4-yl)-2-oxopiperazin-1-yl]acetyl]phenoxyacetate.

The compounds according to the present invention can be formed into salts thereof. Such salts include pharmaceutically acceptable non-toxic salts. The preferred examples include inorganic salts such as sodium, potassium, magnesium or calcium salts; acid addition salts such as trifluoroacetate, hydrochloride, sulfate, acetate, oxalate, citrate, maleate, fumarate or methanesulfonate; amino acid salts such as glutamate or aspartate.

The compounds according to the present invention can be formed into thereof, preferably hydrates or ethanolate.

Furthermore, the compounds represented by the formula (I) may have asymmetric carbons, and the present invention includes all the isomers attributed to the presence of the asymmetric carbons.

Synthesis of the Compounds of the Formula (I)

The compounds according to the present invention can be preferably synthesized by the following methods (A)–(D).

Method (A): Synthesis of the compound wherein W represents the group (a)

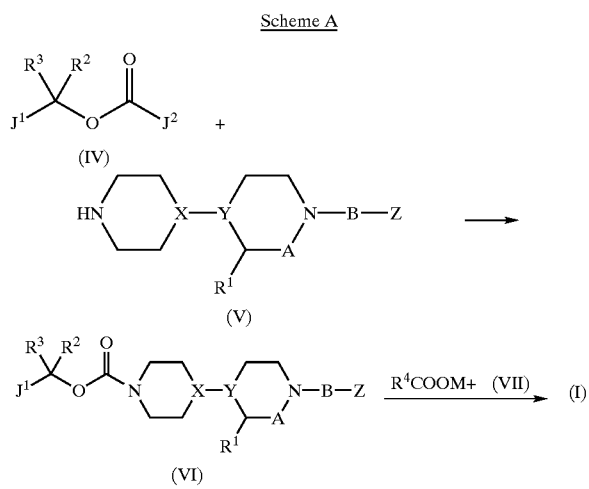

Scheme A in which $R^2$ and $R^3$ have the same meanings as defined in the formula (I), $J^1$ represents a halogen atom or a group which can be easily substituted nucleophilically, $J^2$ represents a halogen atom or substituted phenoxy, X, Y, A, B, Z and $R^1$ have the same meanings as defined in the formula (I), $R^4$ represents $c_{1-10}$ alkyl, $C_{2-10}$ alkenyl, $C_{2-5}$ alkynyl, aryl, or $C_{3-8}$ cycloalkyl, $M^+$ represents a metal ion, for example an ion of alkali or alkaline earth metal such as sodium, potassium, magnesium or calcium, or mercury, silver or zinc.

The method (A) can be carried out according to a manner described in J. Med. Chem., 34, 78 (1991) or Japanese Patent No. 2505728. In particular, the compound (IV) is reacted with the compound (V) in the presence of a base such as trimethylamine, 1,8-bis(dimethylamino)naphtalene, pyridine, potassium carbonate or sodium hydroxide in a halogenated solvent such as dichloromethane or an organic solvent such as diethyl ether, dioxane or tetrahydrofuran at a temperature of –30–35° C., more preferably from 0° C. to room temperature to give the compound (VI).

The compound (VI) thus obtained can be reacted with the compound (VII) $R^4COO^-M^+$ in an alcohol, dimethylformamide or a solvent which is inert to a reactant as an organic acid (e.g., acetic acid or pivalic acid) at a temperature of 0–50° C. to give the compound of the formula (I).

The compound (V) can be synthesized by the method described in WO 96/02503.

Method (B): Synthesis of the compound wherein W represents the group (a)

Scheme B

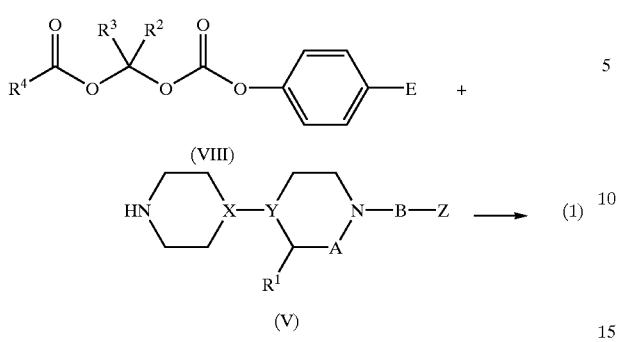

(1)

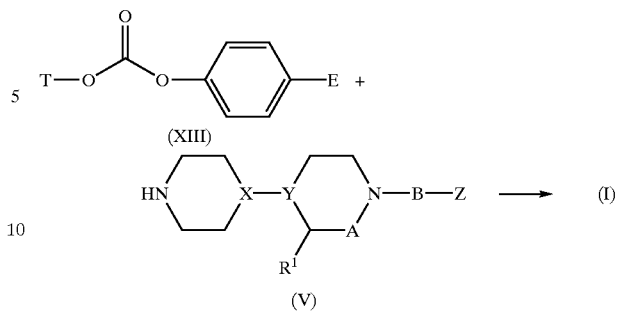

(I)

E represents nitro, halogen, cyano, $C_{1-6}$ alkyl or haloalkyl, and $R^2$, $R^3$, $R^4$, X, Y, A, B, Z and $R^1$ have the same meanings as defined in the formula (I).

The method (B) can be carried out according to a manner described in J. Med. Chem., 31, 318 (1988) or Japanese Patent No. 2510839. In particular, compounds of the formula (I) may be prepared by reacting the compound (VIII) with the compound (V) in the presence of a base such as triethylamine, diethylisopropylamine or proton sponge, or an inorganic base such as potassium carbonate in an aprotic polar solvent such as dimethylformamide, dimethylacetamide or dimethyl sulfoxide at a temperature of 0–40° C., preferably 20–30° C.

The compound (VIII) can be synthesized according to the following scheme:

wherein T represents the group (b) or (c), E has the same meanings as defined in the compound (VIII), and X, Y, A, B, Z and $R^1$ have the same meanings as defined in the formula (I).

The method (C) can be carried out in accordance with a manner described in J. Med. Chem., 39, 480 (1996). In particular, compounds of the formula (I) may be prepared by reacting the compound (XIII) with the compound (V) in the presence of a base such as triethylamine, diethylisopropylamine or proton sponge, or an inorganic base such as potassium carbonate in an aprotic polar solvent such as dimethylformamide, dimethylacetamide or dimethyl sulfoxide at a temperature of 0–40° C., preferably 20–30° C.

The compound (XIII) can be synthesized according to the following scheme:

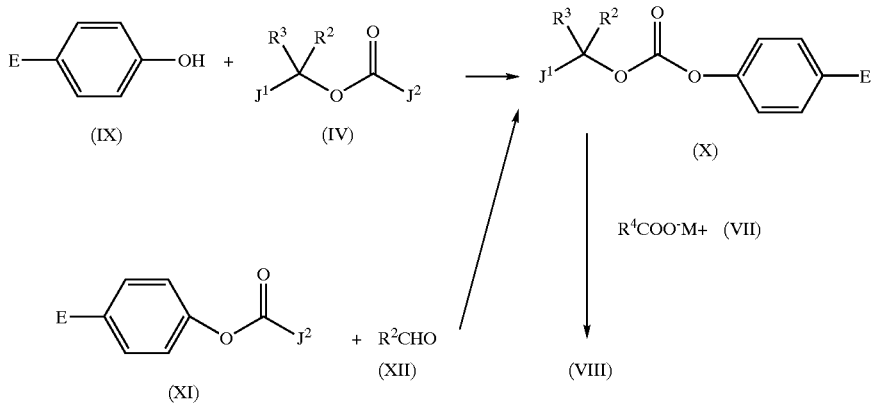

The compound (IX) (wherein E has the same meanings as defined in the formula (VIII)) is reacted with the compound (IV) (wherein $R^2$, $R^3$, $J_1$ and $J_2$ have the same meanings as defined above) in accordance with a manner discribed in J. Med. Chem., 31, 318 (1988) or Japanese Patent No. 2510839. The compound (X) thus obtained can be reacted with the compound (VII): $R^4COO^-M^+$ in accordance with a manner described in the above cited literatures to give the compound (VIII).

The compound (XI) wherein E and $J_2$ have the same meanings as above can be reacted with the compound (XII) wherein $R^2$ has the same meanings as above in accordance with a manner discribed in Synthesis, pp. 407 (1988) to give the compound (X), which is further reacted with the compound (VII) as described above to give the compound (VIII).

Method (C): Synthesis of the compound wherein W represents the group (b) or (c)

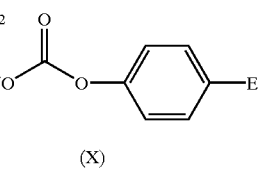

+ ⟶ (XIII)

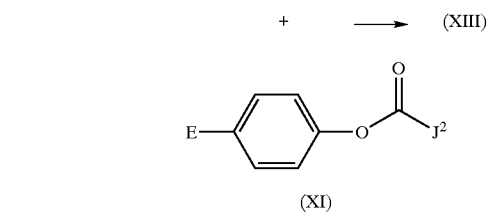

First, the compound (XIV) (wherein T represents the group (b) or (c), and $J^3$ represents a substituent as a leaving group such as a halogen atom, a mesyl group or a tosyl group) is reacted in accordance with a manner described in Synth. Commun., 25, 3875 (1995). The compound (XV) (wherein T has the same meanings as defined above) thus obtained can be reacted with the compound (XI) in accordance with a manner described in J. Med. Chem., 39 480 (1996) to give the compound (XIV).

The compound wherein T represents the group (b) can be synthesized in accordance with the method described in Chem. Pharm. Bull., 32, 2241 (1984).

In addition, the compound wherein T represents the group (c) can be synthesized by the method described in Chem. Pharm. Bull., 31, 2698 (1988).

Method (D): Synthesis of the compound wherein X represents CH, Y represents N, and W represents the group (a)

Scheme D

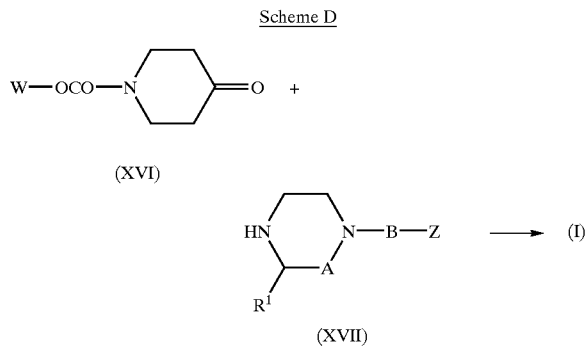

wherein W has the same meanings as defined in the formula (I), and A, B, Z and $R^1$ have the same meanings as defined in the formula (I).

The compound of the formula (I) can be prepared by the reductive aminoalkylation reaction of the compound (XVI) and the compound (XVII) in an inert solvent such as 1,2-dichloroethane, tetrahydrofuran, acetic acid, and ethyl acetate under the catalytic hydrogenation condition in the presence of a hydrogenating metal agent such as sodium cyanoborohydride, lithium cyanoborohydride, sodium borohydride, lithium borohydride or sodium triacetoxyborohydride, or a catalyst such as palladium-carbon, palladium black, palladium hydroxide, platinum oxide or Raney nickel at a temperature of −20–100° C., preferably at 0–70° C. for 0.5–48 hours, preferably 1–24 hours.

The compound (XVI) can be synthesized according to the following scheme:

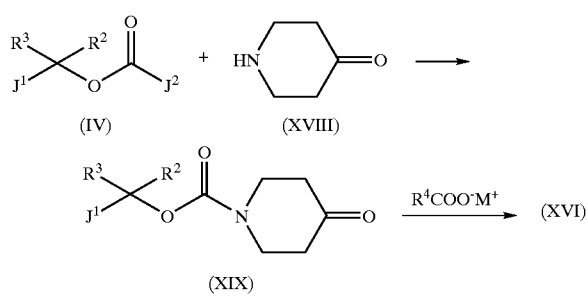

The compound (IV) wherein $R^2$, $R^3$, $J^1$ and $J^2$ have the same meanings as defined above is reacted with the compound (XVIII) in an appropriate solvent, for example a halogenated solvent such as dichloromethane, an organic solvent such as diethyl ether, dioxane or tetrahydrofuran, water, or a mixture thereof in the presence of a base such as triethylamine, proton sponge, pyridine, potassium carbonate, sodium carbonate or sodium hydroxide at a temperature of −30–35° C., preferably at −10–0° C. for 0.5–4 hours, more preferably 0.5–1.5 hours to give the compound (XIX).

The compound (XIX) thus obtained wherein $R^2$, $R^3$ and $J^1$ 1 have the same meanings as defined above and the compound (VII): $R^4COO^-M^+$ prepared above are reacted in an alcohol, N,N-dimethylformamide or a solvent which is inert to a reactant as an organic acid, for example acetic acid or pivalic acid at a temperature of 0–50° C. to give the compound of the formula (XVI).

The compound (XVII) can be synthesized according to the following scheme:

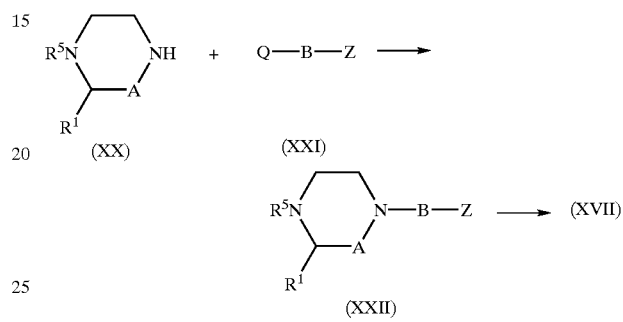

The compound (XX) (wherein $R^5$ represents H or an amino protecting group preferably a t-butoxycarbonyl group or a formyl group, and $R^1$ and A have the same meanings as defined above) and the compound (XXI) (wherein Q represents a halogen atom, lower alkylsulfonyloxy, trifluoromethanesulfonyloxy, or arylsulfonyloxy, and B and Z have the same meanings as defined above) can be reacted in an inert solvent such as dimethylformamide, tetrahydrofuran and a mixed solvent thereof in the presence of a base such as metallic sodium, sodium hydride, calcium hydride, lithium n-butyl, lithium diisopropylamide, or lithium hexamethyldisilazide at a temperature of −80–30° C., preferably 20–30° C. for 10–60 minutes to give the compound (XXII) wherein $R^1$, $R^5$, A, B and Z have the same meanings as defined above. Alternatively, the compound (XX) and the compound (XXI) may be reacted in the presence of a tetraalkylammonium halide as a phase transfer catalyst together with an inorganic base such as sodium hydroxide, potassium hydroxide, sodium carbonate or potassium carbonate at a temperature of 20–150° C., preferably 30–50° C. for 8–72 hours, preferably 12–36 hours.

The compound (XVII) can be obtained by removing the protecting group $R^5$ of the amino group of the compound (XXII) thus obtained, if necessary.

The compound (XX) can also be prepared by the method described in J. Am. Chem. Soc., 62, 1202 (1940).

It is thought apparent to the skilled person in the art that in the preparation procedure described above, the sequence of the synthesis is determined so that no side reactions occur at the functional group which will not participate in the reaction, and the functional groups may be protected with appropriate protecting groups in order to avoid undesirable reactions.

Use of the Compound of the Formula (I) as Pharmaceuticals

The compounds according to the present invention is hydrolyzed in the body to give the compound represented by the general formula (XXIII):

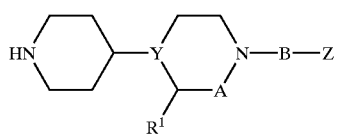

(XXIII)

wherein A, B, X, Y, Z and R' have the same meanings as defined in the formula (I), provided that R represents a hydrogen atom in the group —V—(CH$_2$)$_p$—COOR as D in Z.

The compound inhibits the aggregation of platelets via the inhibition of the bonding of the platelet membrane protein GPIIb/IIIa to fibrinogen. That is to say, the compound of the formula (I) according to the present invention is the so-called prodrug of the compound of the formula (XXIII). In this connection, the compound of the formula (XXIII) may be optionally referred to as the active substance compound of the compound of the formula (I) according to the present invention. The compound of the formula (I) according to the present invention has a higher absorption capacity compared to that of the active substance compound even in its oral administration, and thus has an advantage that it has a high bioavailability in its oral administration. In addition, the compound of the formula (I) is believed to have few side effects such as hemorrhage or low selectivity of function.

The present inventors have also tried to prepare prodrugs from the compounds having the similar activities to those of the active substance compound of the compound (I) according to the present invention and described in WO 94/21599, particularly [[4-[[[(4,5,6,7-tetrahydrothieno[3,2-c]pyridin-2-yl)carbonyl]amino]acetyl ]-o-phenylene]dioxy]diacetic acid by introducing an acetyloxyethoxycarbonyl group in the secondary amine position in the same manner as that in the compound of the formula (I) according to the present invention in accordance with the methods described in J. Alexander et al., J. Med. Chem., 34, 78 (1991), Japanese Patent No. 2505728 or Japanese Patent No. 2510839. That is, diethyl [[4-[[[[5-(1-acetoxyethyl)oxycarbonyl-4,5,6,7-tetrahydrothieno[3,2-c]pyridyl-2-yl]carbonyl]amino] acetyl]-o-phenyl ene]dioxy]-diacetate has been prepared. The compound, however, exhibited no high absorption capacity via its oral administration unlike the case of the compound of the formula (I) according to the present invention. This result is thought to indicate that the compound of the formula (I) according to the present invention has a high oral absorption capacity unexpected by the person skilled in the art.

Thus, the compound of the formula (I) according to the present invention is effective as a therapeutic agent and a prophylactic agent of thrombotic diseases caused by the aggregation of platelets, particularly cerebral infarction, cardiac infarction, angina pectoris, peripheral arterial occlusion, and the like, above all, as a therapeutic agent or a prophylactic agent of these diseases which can be administered orally.

Thus, according to the first embodiment of the present invention there is provided a pharmaceutical composition comprising an effective amount of the compound of the formula (I) according to the present invention or a pharmacologically acceptable salt or solvate thereof together with a pharmacologically acceptable carrier. The pharmaceutical composition is used as a platelet aggregation inhibitor or for the treatment or prophylaxis of thrombotic diseases. More specifically, it is used for the treatment or prophylaxis of cerebral infarction, cardiac infarction, angina pectoris or peripheral arterial occlusion.

Furthermore, according to another embodiment of the present invention, there is provided a therapeutic or prophylactic method of thrombotic diseases comprising administering an effective amount of the compound of the formula (I) according to the present invention or a pharmacologically acceptable salt or solvate thereof to animals including human.

According to a further embodiment of the present invention, there are provided the use of the compound of the formula (I) according to the present invention or a pharmacologically acceptable salt or solvate thereof for the therapy or prophylaxis of thrombotic diseases, and the use of the compound of the formula (I) according to the present invention or a pharmacologically acceptable salt or solvate thereof for preparing the therapeutic or prophylactic agents of thrombotic diseases.

The compound according to the present invention, which may be administered directly as the compound, is preferably administered in the form of a pharmaceutical composition comprising the compound according to the present invention as an effective component. The pharmaceutical composition can be prepared in appropriate dosage forms depending on the dosage routes, specifically in either one of the dosage forms such as oral agents, e.g. especially tablets, capsules, granules, powder, pills, fine particles or troches, rectal agents, oily suppositories, aqueous suppositories, or the like.

A variety of these preparations can be prepared by the conventional method with excipients, fillers, bonding agents, humidifying agents, disproportionating agents, surface active agents, lubricating agents, dispersing agents, buffers, preservatives, dissolving aids, antiseptic agents, flavoring agents, analgesic agents, stabilizing agents, and the like. The non-toxic acceptable additives described above include for example lactose, fructose, glucose, starch, gelatin, magnesium carbonate, synthetic magnesium silicate, talc, magnesium stearate, methyl cellulose or a salt thereof, gum arabic, polyethylene glycol, syrup, petrolatum, glycerol, ethanol, propylene glycol, citric acid, sodium chloride, sodium sulfite, sodium phosphate, and the like.

The content of the compounds of the present invention in the pharmaceutical composition depends on their dosage forms, and is generally in the range of 1–70% by weight, preferably about 5–50% by weight of the total composition.

The dose is determined appropriately in consideration of the use, the age and sex of the patient and the severity of the condition, and for the treatment of thrombotic diseases the compound is administered generally in an amount of about 0.1–1,000 mg, preferably 1–200 mg per day for an adult, which can be administered once or in several sub-divided portions.

EXAMPLES

The present invention is described in detail below with reference to the following Examples and Test Examples, but it should not be construed to be limited thereto.

Preparation 1

Diethyl [[4-[[[[5-(1-Acetoxyethyl)oxycarbonyl-4,5,6,7-tetrahydrothieno[3,2-c]pyridin-2-yl]carbonyl]amino]-acetyl]-o-phenylene]dioxy]diacetate To a suspension of 126 mg of diethyl [[4-[[[(4,5,6,7-tetrahydrothieno[3,2-c]pyridin-2-yl)carbonyl]amino] acetyl]-o-phenylen]dioxy]diacetate synthesized according to the method described in WO 9421599 in 3 ml of N,N-dimethylformamide was added 105 mg of 1-acetoxyethyl 4-nitrophenyl carbonate under stirring at room temperature, and the mixture was stirred at 40° C. for 20 hours. The reaction was poured into 3 ml of water, and extracted with 5 ml of ethyl acetate. The separated organic layer was dried over magnesium sulfate, and the solvent was removed by distillation. The residue thus obtained was purified by chromatography on an LH-20 column (chloroform:methanol=1:1) and a silica gel column (chloroform:acetone=8:1) to give the title compound (25.8 mg, 16%) as a free base.

$^1$H-NMR (CDCl$_3$) δ: 1.23–1.35 (6H, m), 1.50–1.58 (3H, m), 2.08 (3H, s), 2.90 (2H, brs), 3.79 (2H, brs), 4.20–4.33 (4H, m), 4.56 (2H, brs), 4.70–4.86 (6H, m), 6.80–6.93 (2H, m), 6.98 (1H, brs), 7.32 (1H, brs), 7.55 (1H, brs), 7.60–7.68 (1H, m). FABMS (m/z): 635 (M+H$^+$).

Example 1

Ethyl 4-[[4-(1-Acetoxymethoxycarbonylpiperidin-4-yl)-2-oxopiperazin-1-yl]acetyl]phenoxyacetate a) To a suspension of 10.2 g of ethyl 4-[[2-oxo-4-(piperidin-4-yl)-piperazin-1-yl]acetyl]phenoxyacetate dihydrochloride synthesized according to the method described in WO 962503 in 100 ml of methylene chloride were added dropwise 9.5 ml of triethylamine and 2.3 ml of chloromethyl chloroformate with stirring at 0° C., and the mixture was stirred at 0° C. for 2 hours. The reaction mixture thus obtained was poured into 100 ml of 20% aqueous sodium hydroxide solution, and extracted three times with 200 ml of ethyl acetate.

The organic layer separated was dried over magnesium sulfate, and evaporated to give 10.6 g of ethyl 4-[[4-(1-chloromethoxycarbonylpiperidin-4-yl)-2-oxopiperazin-1-yl]acetyl]phenoxyacetate as a crude crystalline product.

b) To a solution of 10.6 g of the compound obtained in the step a) in 100 ml of N,N-dimethylformamide were 1.5 ml of acetic acid and 3.28 g of potassium carbonate with stirring at room temperature, and the mixture was stirred at 40° C. for 3 hours. The reaction mixture was poured into 100 ml of 200 ml of 20% aqueous sodium hydroxide, and extracted three times with 200 ml of ethyl acetate. The organic layer separated was washed five times with 50 ml of 20% aqueous sodium hydroxide solution, dried over magnesium sulfate, and evaporated. The residue thus obtained was purified by recrystallization from ethanol-diisopropyl ether to give the title compound (9.99 g, 90%) as a free base.

$^1$H-NMR (CDCl$_3$) δ: 1.30 (3H, t, J=7.2 Hz), 1.40–1.55 (2H, m), 1.78–1.94 (2H, m), 2.12 (3H, s), 2.51 (1H, tt, J=11.0 Hz, 3.4 Hz), 2.75–3.00 (4H, m), 3.37 (2H, s), 3.38 (2H, t, J=5.2 Hz), 4.18 (2H, dd, J=38.4 Hz, 13.6 Hz), 4.28 (2H, q, J=7.2 Hz), 4.69 (2H, s), 4.78 (2H, s), 5.76 (2H, s), 6.96 (2H, d, J=8.8 Hz), 7.95 (2H, d, J=8.8 Hz). FABMS (m/z): 520 (M+H$^+$).

Example 2

Isopropyl 4-[[4-(1-Acetoxymethoxycarbonylpiperidin-4-yl)-2-oxopiperazin-1-yl]acetyl]phenoxyacetate Hydrochloride a) Isopropyl 4-[[4-(1-chloromethoxycarbonyl-piperidin-4-yl)-2-oxopiperazin-1-yl]acetyl]phenoxyacetate was obtained as a crude crystal (180 mg) in the same manner as in Example 1a) from 150 mg of isopropyl 4-[[2-oxo-4-(piperidin-4-yl)piperazin-1-yl]acetyl]phenoxyacetate dihydrochloride synthesized according to the method described in WO 962503 in the same manner as in Example 1a) except that methylene chloride and chloromethyl chloroformate were used in an amount of 3 ml and 30 μl, resepectively, and triethylamine was replaced by 210 mg of proton sponge.

$^1$H-NMR (CDCl$_3$) δ: 1.28 (6H, d, J=6.3 Hz), 1.40–1.60 (2H, m), 1.80–1.95 (2H, m), 2.52–2.60 (1H, m), 2.79–3.00 (5H, m), 3.30–3.40 (4H, m), 4.05–4.30 (2H, m), 4.66 (2H, s), 4.78 (2H, s), 5.15 (1H, sept, J=6.3 Hz), 5.79 (2H, brs), 6.95 (2H, d, J=8.9 Hz), 7.95 (2H, d, J=8.9 Hz). TSPMS (m/z): 510 (M+H$^+$).

b) The title compound was obtained as a free base (124 mg) from 156 mg of the compound obtained in the step a) in the same manner as in Example 1b) except that N,N-dimethylformamide and acetic acid were used in an amount of 3.5 ml and 53 μl, respectively, and potassium carbonate was replaced by 110 mg of cesium carbonate.

c) To a solution of 124 mg of the compound prepared in the step b) in 2 ml of ethanol were added 246 μl of 1N hydrochloric acid and 5 ml of water. The mixture was then concentrated under reduced pressure, and lyophilized to give the title compound (124 mg, 71.4%).

$^1$H-NMR (D$_2$O) δ: 1.32 (6H, d, J=6.4 Hz), 1.73–1.85 (2H, m), 2.12 (3H, s), 2.28 (2H, brs), 2.96–3.04 (2H, m), 3.60–3.75 (1H, m), 3.80 (4H, brs), 4.17 (2H, s), 4.34 (2H, brs), 4.93 (2H, s), 5.09 (2H, s), 5.18 (1H, sept, J=6.4 Hz), 5.80 (2H, s), 7.15 (2H, d, J=9.0 Hz), 8.07 (2H, d, J=9.0 Hz). TSPMS (m/z): 534 (M+H$^+$).

Example 3

Cyclohexyl 4-[[4-(1-Acetoxymethoxycarbonylpiperidin-4-yl)-2-oxopiperazin-1-yl]acetyl]phenoxyacetate Hydrochloride a) Cyclohexyl 4-[[4-(1-chloromethoxycarbonylpiperidin-4-yl)-2-oxopiperazin-1-yl]acetyl]phenoxyacetate was obtained in an amount of 166 mg as a crude crystalline product from 160 mg of cyclohexyl 4-[[2-oxo-4-(piperidin-4-yl)piperazin-1-yl]acetyl]phenoxyacetate dihydrochloride synthesized according to the method described in WO962503 in the same manner as in Example 1a) except that methylene chloride, triethylamine and chloromethyl chloroformate were used in an amount of 3.2 ml, 134 μl and 30 μl, respectively.

$^1$H-NMR (CDCl$_3$) δ: 1.20–2.00 (13H, m), 2.47–2.58 (1H, m), 2.80–3.00 (5H, m), 3.30–3.40 (4H, m), 4.05–4.30 (2H, m), 4.68 (2H, s), 4.78 (2H, s), 4.84–4.96 (1H, m), 5.79 (2H, brs), 6.95 (2H, d, J=8.9 Hz), 7.95 (2H, d, J=8.9 Hz).

b) The title compound was obtained in an amount of 117 mg as a free base from 166 mg of the compound prepared in the step b) in the same manner as in Example 1b) except that N,N-dimethylformamide and acetic acid were used in an amount of 3.5 ml and 52 μl, respectively, and potassium carbonate was replaced by 108 mg of cesium carbonate.

c) To a solution of 117 mg of the compound prepared in the step b) in 3 ml of ethanol were added 205 μl of 1N hydrochloric acid, followed by 4 ml of water. The solution was then concentrated under reduced pressure, and lyophilized to give the title compound (120.5 mg, 65.5%).

$^1$H-NMR (D$_2$O) δ: 1.30–1.62 (6H, m), 1.63–1.94 (6H, m), 2.19 (3H, s), 2.20–2.40 (2H, m), 2.95–3.00 (1H, m), 3.70–3.80 (1H, m), 3.83 (4H, brs), 4.20 (2H, s), 4.27–4.42 (2H, m), 4.94 (2H, s), 5.09 (2H, s), 5.79 (2H, s), 7.15 (2H, d, J=9.0 Hz), 8.07 (2H, d, J=9.0 Hz). TSPMS (m/z): 574 (M+H$^+$).

Example 4

2,2,2-Trichloroethyl 4-[[4-(1-acetoxymethoxycarbonylpiperidin-4-yl)-2-oxopiperazin-1-yl]acetyl]phenoxyacetate The title compound was obtained in an amount of 1.35 g (66%) from 2.98 g of 2,2,2-trichloroethyl 4-[[2-oxo-4-

(piperidin-4-yl)piperazin-1-yl]acetyl]phenoxyacetate dihydrochloride in the same manner as in Example 1.

$^1$H-NMR (CDCl$_3$) δ: 1.35–1.60 (2H, m), 1.75–1.95 (2H, m), 2.12 (3H, s), 2.52 (1H, tt, J=10.8 Hz, 3.6 Hz), 2.80–2.95 (4H, m), 3.37 (2H, s), 3.38 (2H, t, J=5.2 Hz), 4.18 (2H, dd, J=37.2 Hz, 12.8 Hz), 4.78 (2H, s), 4.87 (2H, s), 4.88 (2H, s), 5.76 (2H, s), 6.99 (2H, d, J=8.6 Hz), 7.96 (2H, d, J=8.6 Hz). FABMS (m/z): 622 (M+H$^+$).

Example 5

4-[[4-(1-Acetoxymethoxycarbonylpiperidin-4-yl)-2-oxopiperazin-1-yl]acetyl]phenoxyacetic Acid To a solution of 77.5 mg of the compound prepared Example 4 in 2 ml of acetic acid was added zinc dust with stirring at room temperature, and the mixture was stirred for 3 hours. The reaction mixture was filtered through celite, and the filtrate was concentrated under reduced pressure. The residue thus obtained was dissolved in 5 ml of 0.1N aqueous hydrochloric acid solution, and purified by chromatography on an HP-20 column (eluent: 5% aqueous acetone solution) to give 34.1 mg of the title compound (56%).

$^1$H-NMR (D$_2$O) δ: 1.30–1.48 (2H, m), 1.85–2.00 (2H, m), 1.99 (3H, s), 2.70–2.98 (3H, m), 3.10 (2H, t, J=5.4 Hz), 3.41 (2H, t, J=5.4 Hz), 3.50 (2H, s), 3.95–4.17 (2H, m), 4.45 (2H, s), 4.82 (2H, s), 5.59 (2H, s), 6.90 (2H, d, J=9.0 Hz), 7.86 (2H, d, J=9.0 Hz). FABMS (m/z): 492 (M+H$^+$).

Example 6 n-Butyl 4-[[4-[1-(1-Acetoxyethyl)oxycarbonylpiperidin-4-yl]-2-oxopiperazin-1-yl]acetyl]phenoxyacetate a) To a suspension of 99.6 mg of n-butyl 4-[[2-oxo-4-(piperidin-4-yl)-piperazin-1-yl]acetyl]phenoxyacetate dihydrochloride synthesized according to the method described in WO962503 in 2 ml of methylene chloride were added 151 mg of proton sponge and 26 μl of 1-chloroethyl chloroformate with stirring at 0° C., and the mixture was stirred at room temperature for 18 hours. The reaction mixture thus obtained was poured into 2 ml of water, and extracted three times with 4 ml of ethyl acetate. The organic layer collected was dried over magnesium sulfate, and the solvent was removed by distillation to give 82.7 mg of n-butyl 4-[[4-[1-(1-chloroethyl)oxycarbonylpiperidin-4-yl]-2-oxopiperazin-1-yl]acetyl]phenoxyacetate as a crude crystalline product.

b) To a solution of 73.7 mg of the compound obtained in the above step a) in 2 ml of acetic acid was added 76.7 mg of mercury acetate with stirring at room temperature, and the mixture was stirred at room temperature for 3 days. The reaction mixture was concentrated under reduced pressure, and the residue thus obtained was pulverized with 5 ml of a 20% aqueous sodium hydroxide solution and extracted three times with 5 ml of ethyl acetate.

The organic layer separated was dried over magnesium sulfate, and the solvent was removed by distillation. The residue obtained was purified on a silica gel column (chloroform:methanol=20:1) to give 75.4 mg of the title compound (76%).

$^1$H-NMR (CDCl$_3$) δ: 0.93 (3H, t, J=7.6 Hz), 1.30–1.70 (6H, m), 1.49 (3H, d, J=5.5 Hz), 1.80–1.90 (2H, m), 2.07 (3H, s), 2.45–2.55 (1H, m), 2.75–2.97 (4H, m), 3.38 (2H, s), 3.38 (2H, t, J=5.6 Hz), 4.05–4.25 (2H, m), 4.22 (2H, t, J=6.6 Hz), 4.69 (2H, s), 4.78 (2H, s), 6.81 (1H, q, J=5.5 Hz), 6.95 (2H, d, J=9.0 Hz), 7.95 (2H, d, J=9.0 Hz). TSPMS (m/z): 562 (M+H$^+$).

Example 7

Benzyl 4-[[4-[1-(1-Acetoxyethyl)oxycarbonylpiperidin-4-yl]-2-oxopiperazin-1-yl]acetyl]phenoxyacetate The title compound was prepared in an amount of 251 mg (50 mg) from 467 mg of benzyl 4-[[2-oxo-4-(piperidin-4-yl)piperazin-1-yl]-acetyl]phenoxyacetate dihydrochloride in the same manner as in Example 6.

$^1$H-NMR (CDCl$_3$) δ: 1.40–1.60 (2H, m), 1.49 (3H, d, J=5.4 Hz), 1.80–1.90 (2H, m), 2.07 (3H, s), 2.45–2.55 (1H, m), 2.75–2.95 (4H, m), 3.30–3.45 (4H, m), 4.00–4.30 (2H, m), 4.73 (2H, s), 4.77 (2H, s), 5.24 (2H, s), 6.81 (1H, q, J=5.4 Hz), 6.93 (2H, d, J=9.0 Hz), 7.30–7.40 (5H, m), 7.93 (2H, d, J=9.0 Hz). TSPMS (m/z): 613 (M+NH$_4^+$).

Example 8

Ethyl 4-[[4-[1-(1-Acetoxyethyl)oxycarbonylpiperidin-4-yl]-2-oxopiperazin-1-yl]acetyl]phenoxyacetate To a suspension of 107 mg of ethyl 4-[[2-oxo-4-(piperidin-4-yl)piperazin-1-yl]acetyl]phenoxyacetate dihydrochloride synthesized according to the method described in WO962503 in 2 ml of N,N-dimethylformamide were added 110 mg of proton sponge and 85.7 mg of 1-acetoxyethyl 4-nitrophenyl carbonate with stirring at 0° C., and the mixture was stirred at room temperature for 18 hours. The reaction mixture was poured into 2 ml of water and extracted three times with 4 ml of ethyl acetate. The organic layer was dried over magnesium sulfate, and the solvent was removed by distillation. The residue thus obtained was purified by chromatography on an LH-20 column (chloroform:methanol=1:1) to give 119 mg of the title compound (100%).

$^1$H-NMR (CDCl$_3$) δ: 1.30 (3H, t, J=7.1 Hz), 1.40–1.60 (2H, m), 1.49 (3H, d, J=5.6 Hz), 1.75–1.90 (2H, m), 2.07 (3H, s), 2.45–2.55 (1H, m), 2.75–2.95 (4H, m), 3.36 (2H, s), 3.38 (2H, t, J=5.4 Hz), 4.00–4.30 (2H, m), 4.28 (2H, q, J=7.1 Hz), 4.69 (2H, s), 4.77 (2H, s), 6.81 (1H, q, J=5.6 Hz), 6.95 (2H, d, J=8.8 Hz), 7.95 (2H, d, J=8.8 Hz). TSPMS (m/z): 534 (M+H$^+$).

Example 9

Cyclohexyl 4-[[4-[1-(1-Acetoxyethyl)oxycarbonylpiperidin-4-yl]-2-oxopiperazin-1-yl]acetyl]phenoxyacetate The title compound was obtained in an amount of 113 mg (100%) from 102 mg of cyclohexyl 4-[[2-oxo-4-(piperidin-4-yl)piperazin-1-yl]acetyl]phenoxyacetate dihydrochloride in the same manner as in Example 8. $^1$H-NMR (CDCl$_3$) δ: 1.20–1.90 (14H, m), 1.49 (3H, d, J=5.5 Hz), 2.07 (3H, s), 2.45–2.55 (1H, m), 2.75–2.95 (4H, m), 3.36 (2H, s), 3.38 (2H, t, J=5.2 Hz), 4.05–4.25 (2H, m), 4.67 (2H, s), 4.77 (2H, s), 4.85–4.95 (1H, m), 6.81 (1H, q, J=5.5 Hz), 6.95 (2H, d, J=9.0 Hz), 7.95 (2H, d, J=9.0 Hz). FABMS (m/z): 588 (M+H$^+$).

Example 10

1-Methylpentyl 4-[[4-[1-(1-Acetoxyethyl)oxycarbonylpiperidin-4-yl]-2-oxopiperazin-1-yl]acetyl]phenoxyacetate The title compound was obtained in an amount of 131 mg (100%) from 119 mg of 1-methylpentyl 4-[[2-oxo-4-(piperidin-4-yl)piperazin-1-yl]acetyl]-phenoxyacetate dihydrochloride.

¹H-NMR (CDCl₃) δ: 0.88 (3H, t, J=6.8 Hz), 1.15–1.65 (8H, m), 1.25 (3H, d, J=6.4 Hz), 1.49 (3H, d, J=5.4 Hz), 1.78–1.90 (2H, m), 2.07 (3H, s), 2.45–2.55 (1H, m), 2.75–2.95 (4H, m), 3.36 (2H, s), 3.38 (2H, t, J=5.2 Hz), 4.05–4.25 (2H, m), 4.67 (2H, s), 4.77 (2H, s), 4.98–5.09 (1H, m), 6.81 (1H, q, J=5.4 Hz), 6.95 (2H, d, J=8.8 Hz), 7.95 (2H, d, J=8.8 Hz). FABMS (m/z): 590 (M+H⁺).

Example 11

Isopropyl 4-[[4-[1-(1-Acetoxyethyl)oxycarbonylpiperidin-4-yl]-2-oxopiperazin-1-yl]acetyl]phenoxyacetate The title compound was obtained in a yield of 105 mg (99%) from 95.2 mg of isopropyl 4-[[2-oxo-4-(piperidin-4-yl)-piperazin-1-yl]acetyl]phenoxyacetate dihydrochloride in the same manner as in Example 8.

¹H-NMR (CDCl₃) δ: 1.28 (6H, d, J=6.4 Hz), 1.40–1.55 (2H, m), 1.49 (3H, d, J=5.5 Hz), 1.80–1.90 (2H, m), 2.07 (3H, s), 2.45–2.55 (1H, m), 2.75–2.95 (4H, m), 3.36 (2H, s), 3.38 (2H, t, J=5.4 Hz), 4.05–4.25 (2H, m), 4.66 (2H, s), 4.78 (2H, s), 5.14 (1H, sept, J=6.2 Hz), 6.81 (1H, q, J=5.5 Hz), 6.95 (2H, d, J=8.8 Hz), 7.95 (2H, d, J=8.8 Hz). TSPMS (m/z): 548 (M+H⁺).

Example 12

Methyl 4-[[4-[1-(1-Acetoxyethyl)oxycarbonylpiperidin-4-yl]-2-oxopiperazin-1-yl]acetyl]phenoxyacetate The title compound was obtained in a yield of 362 mg (100%) from 362 mg of methyl 4-[[2-oxo-4-(piperidin-4-yl)piperazin-1-yl]acetyl]phenoxyacetate dihydrochloride in the same manner as in Example 8.

¹H-NMR (CDCl₃) δ: 1.40–1.55 (2H, m), 1.49 (3H, d, J=5.4 Hz), 1.78–1.90 (2H, m), 2.07 (3H, s), 2.45–2.55 (1H, m), 2.75–2.95 (4H, m), 3.36 (2H, s), 3.38 (2H, t, J=5.4 Hz), 3.82 (3H, s), 4.00–4.28 (2H, m), 4.71 (2H, s), 4.77 (2H, s), 6.81 (1H, q, J=5.4 Hz), 6.95 (2H, d, J=9.0 Hz), 7.96 (2H, d, J=9.0 Hz). TSPMS (m/z): 520 (M+H⁺).

Example 13

Tetrahydro-4H-pyran-4-yl 4-[[4-[1-(1-Acetoxyethyl)oxycarbonylpiperidin-4-yl]-2-oxopiperazin-1-yl]acetyl]phenoxyacetate The title compound was obtained in a yield of 105 mg (100%) from 94.8 mg of tetrahydro-4H-pyran-4-yl 4-[[2-oxo-4-(piperidin-4-yl)piperazin-1-yl]acetyl]phenoxyacetate dihydrochloride in the same manner as in Example 8.

¹H-NMR (CDCl₃) δ: 1.40–1.55 (2H, m), 1.49 (3H, d, J=5.4 Hz), 1.63–2.00 (6H, m), 2.07 (3H, s), 2.45–2.56 (1H, m), 2.75–2.95 (4H, m), 3.37 (2H, s), 3.38 (2H, t, J=5.4 Hz), 3.53 (2H, ddd, J=11.9 Hz, 8.9 Hz, 2.9 Hz), 3.87 (2H, ddd, J=11.9 Hz, 4.8 Hz, 4.4 Hz), 4.05–4.25 (2H, m), 4.71 (2H, s), 4.77 (2H, s), 5.09 (1H, tt, J=8.6 Hz, 4.3 Hz), 6.81 (1H, q, J=5.4 Hz), 6.96 (2H, d, J=9.2 Hz), 7.96 (2H, d, J=9.2 Hz). TSPMS (m/z): 590 (M+H⁺).

Example 14

1,3-bis(Ethyloxy)propan-2-yl 4-[[4-[1-(1-Acetoxyethyl)oxycarbonylpiperidin-4-yl]-2-oxopiperazin-1-yl]acetyl]phenoxyacetate The title compound was obtained in a yield of 114 mg (100%) from 109 mg of 1,3-bis(ethyloxy)propan-2-yl 4-[[2-oxo-4-(piperidin-4-yl)-piperazin-1-yl]acetyl]phenoxyacetate dihydrochloride in the same manner as in Example 8.

¹H-NMR (CDCl₃) δ: 1.18 (6H, t, J=7.0 Hz), 1.40–1.55 (2H, m), 1.49 (3H, d, J=5.6 Hz), 1.78–1.90 (2H, m), 2.07 (3H, s), 2.45–2.55 (1H, m), 2.75–2.95 (4H, m), 3.36 (2H, s), 3.37 (2H, t, J=5.2 Hz), 3.48 (2H, dq, J=9.3 Hz, 7.0 Hz), 3.53 (2H, dq, J=9.3 Hz, 7.0 Hz), 3.59 (4H, d, J=5.2 Hz), 4.00–4.30 (2H, m), 4.74 (2H, s), 4.77 (2H, s), 5.28 (1H, quint, J=5.2 Hz), 6.81 (1H, q, J=5.6 Hz), 6.96 (2H, d, J=9.2 Hz), 7.94 (2H, d, J=9.2 Hz). TSPMS (m/z): 636 (M+H⁺).

Example 15

N,N-dimethylcarbamoylmethyl 4-[[4-[1-(1-Acetoxyethyl)oxycarbonylpiperidin-4-yl]-2-oxopiperazin-1-yl]acetyl]phenoxyacetate a) To solution of 300 mg of 4-[[4-(1-t-butyloxycarbonylpiperidin-4-yl)-2-oxopiperazin-1-yl]acetyl]phenoxyacetic acid Na salt synthesized according to the method described in WO962503 and 108 mg of potassium carbonate in 4 ml of dimethylformamide was added 88 mg of N,N-dimethylchloroacetamide, and the mixture was stirred at 80° C. for 2 hours. The reaction mixture was diluted with ethyl acetate and water, and the organic layer was separated. The aqueous layer was extracted with ethyl acetate. The organic layer separated was washed with saturated aqueous saline, dried over sodium sulfate, and evaporated. The residue was purified by PTLC (Merck 5744, developing agent:methylene chloride:methanol=15:1, eluent:methylene chloride:methanol=5:1) to give 146 mg (43%) of N,N-dimethylcarbamoylmethyl 4-[[4-(1-t-butyloxycarbonylpiperidin-4-yl)-2-oxopiperazin-1-yl]acetyl]phenoxyacetate.

¹H-NMR (CDCl₃) δ: 1.37–1.50 (2H, m), 1.46 (9H, s), 1.83 (2H, brd, J=12.0 Hz), 2.42–2.52 (1H, m), 2.70–2.90 (4H, m), 2.97 (3H, m), 2.98 (3H, s), 3.34–3.40 (4H, m), 4.13 (2H, brs), 4.77 (2H, s), 4.85 (2H, s), 4.87 (2H, s), 7.03 (2H, d, J=9.0 Hz), 7.96 (2H, d, J=9.0 Hz). TSPMS (m/z): 561 (M+H⁺).

b) To a solution of 146 mg of the compound obtained in the above step a) in 2.6 ml of dioxane was 0.65 ml of 4N hydrochloric acid, and the mixture was stirred at room temperature for 6 hours. The reaction mixture was diluted with ethyl acetate, and the crystals precipitated was collected by filtration to give 136 mg of N,N-dimethylcarbamoylmethyl 4-[[2-oxo-4-(piperidin-4-yl)piperazin-1-yl]acetyl]phenoxyacetate hydrochloride (98%).

¹H-NMR (D₂O) δ: 1.83–2.00 (2H, m), 2.38 (2H, brd, J=13 Hz), 2.84 (3H, s), 2.91 (3H, s), 3.05 (3H, brt, J=12.0 Hz), 3.54–3.71 (7H, m), 3.99–4.07 (2H, m), 4.91 (2H, s), 4.95 (4H, s), 7.04 (2H, d, J=9.0 Hz), 7.93 (2H, d, J=9.0 Hz). TSPMS (m/z): 461 (M+H⁺).

c) The title compound was prepared in a yield of 83 mg (64%) from 117 mg of the compound obtained in the above step b) in the same manner as in Example 8 except that dimethylformamide, proton sponge and 1-acetoxyethyl 4-nitrophenylcarbonate were used in an amount of 2.2 ml, 104 mg and 71 mg, respectively, and purification was carried out by chromatography on a DIAION LH-20 column (methylene chloride:methanol=1:1) followed by PTLC (Merck 5744, developing agent:methylene chloride:methanol=20:1, eluent:methylene chloride:methanol=5:1).

¹H-NMR (CDCl₃) δ: 1.40–1.60 (2H, m), 1.49 (3H, d, J=5.6 Hz), 1.85 (2H, brd, J=12.0 Hz), 2.07 (3H, s), 2.46–2.54 (1H, m), 2.85 (4H, brs), 2.97 (3H, s), 2.98 (3H, s), 3.33–3.40 (4H, m), 4.15 (2H, brs), 4.77 (2H, s), 4.85 (2H, s), 4.87 (2H, s), 6.81 (1H, q, J=5.6 Hz), 7.03 (2H, d, J=9.0 Hz), 7.96 (2H, d, J=9.0 Hz). TSPMS (m/z): 591 (M+H⁺).

Example 16

Ethyl 4-[[4-[1-(1-Acetoxypropyl)oxycarbonylpiperidin-4-yl]-2-oxopiperazin-1-yl]acetyl]phenoxyacetate Hydrochloride a) The title compound was prepared in a yield of 115 mg (100%) as a free base from 101 mg of ethyl 4-[[2-oxo-4-(piperidin-4-yl)piperazin-1-yl]acetyl]phenoxyacetate dihydrochloride synthesized according to the method described in WO962503 in the same manner as in Example 8 except that N,N-dimethylformamide, proton sponge and 1-acetoxypropyl 4-nitrophenyl carbonate were used in an amount of 2 ml, 101 mg and 82.8 mg, respectively.

b) The title compound was obtained in an amount of 112 mg (90%) as the hydrochloride by adding dropwise 0.2 ml of a 1N aqueous hydrochloric acid solution to a solution of 115 mg of the compound obtained in the above step a) in 2 ml of dioxane and then lyophilizing the reaction mixture.

¹H-NMR (D₂O) δ: 0.80 (3H, t, J=7.4 Hz), 1.13 (3H, t, J=7.0 Hz), 1.45–1.65 (2H, m), 1.65–1.78 (2H, m), 1.97 (3H, s), 2.05 (2H, brs), 2.74–2.92 (3H, m), 3.50–3.65 (4H, m), 3.91 (2H, brs), 4.05–4.23(2H, m), 4.15 (2H, q, J=7.0 Hz), 4.76 (2H, s), 4.89 (2H, s), 6.46 (1H, brs), 6.96 (2H, d, J=9.0 Hz), 7.87 (2H, d, J=9.0 Hz).

Example 17

Ethyl 4-[[4-[1-(1-Acetoxy-2-methylpropyl)oxycarbonylpiperidin-4-yl]-2-oxopiperazin-1-yl]acetyl]phenoxyacetate The title compound was obtained in an amount of 123 mg (100%) from 104 mg of ethyl 4-[[2-oxo-4-(piperidin-4-yl)piperazin-1-yl]acetyl]phenoxyacetate dihydrochloride synthesized according to the method described in WO962503 in the same manner as in Example 8 except that N,N-dimethylformamide, proton sponge and 1-acetoxy-2-methylpropyl 4-nitrophenyl carbonate were used in an amount of 2 ml, 103 mg and 95.5 mg, respectively. ¹H-NMR (CDCl₃) δ: 0.97 (3H, d, J=6.8 Hz), 0.98 (3H, d, J=6.8 Hz), 1.30 (3H, t, J=7.2 Hz), 1.40–1.55 (2H, m), 1.78–1.90 (2H, m), 1.98–2.12 (1H, m), 2.08 (3H, s), 2.45–2.55 (1H, m), 2.86 (4H, brs), 3.37 (2H, s), 3.38 (2H, t, J=6.0 Hz), 4.05–4.28 (2H, m), 4.28 (2H, q, J=7.2 Hz), 4.69 (2H, s), 4.77 (2H, s), 6.60 (1H, d, J=4.8 Hz), 6.96 (2H, d, J=9.2 Hz), 7.95 (2H, d, J=9.2 Hz). TSPMS (m/z): 562 (M+H⁺).

Example 18

Tetrahydro-4H-pyran-4-yl 4-[[4-[1-(1-Acetoxy-2-methylpropyl)oxycarbonylpiperidin-4-yl]-2-oxopiperazin-1-yl]acetyl]phenoxyacetate The title compound was obtained in a yield of 110 mg (100%) from 94 mg of tetrahydro-4H-pyran-4-yl 4-[[2-oxo-4-(piperidin-4-yl)-piperazin-1-yl]acetyl]phenoxyacetate dihydrochloride in the same manner as in Example 8.

¹H-NMR (CDCl₃) δ: 0.97 (3H, d, J=7.2 Hz), 0.98 (3H, d, J=6.8 Hz), 1.35–1.55 (2H, m), 1.69 (2H, dddd, J=13.0 Hz, 9.0 Hz, 8.9 Hz, 4.1 Hz), 1.78–2.15 (5H, m), 2.08 (3H, s), 2.45–2.57 (1H, m), 2.86 (4H, brs), 3.37 (2H, s), 3.38 (2H, t, J=5.2 Hz), 3.53 (2H, ddd, J=12.2 Hz, 9.0 Hz, 3.0 Hz), 3.87 (2H, ddd, J=12.2 Hz, 5.2 Hz, 4.1 Hz), 4.05–4.27 (2H, m), 4.71 (2H, s), 4.78 (2H, s), 5.09 (1H, quint, J=4.3 Hz), 6.60 (1H, d, J=5.2 Hz), 6.96 (2H, d, J=9.0 Hz), 7.96 (2H, d, J=9.0 Hz). TSPMS (m/z): 618 (M+H⁺).

Example 19

Isopropyl 4-[[4-[1-(1-Acetoxy-2-methylpropyl)oxycarbonylpiperidin-4-yl]-2-oxopiperazin-1-yl]acetyl]phenoxyacetate Hydrochloride a) The title compound was obtained in a yield of 148 mg (88.2%) as a free base from 150 mg of isopropyl 4-[[2-oxo-4-(piperidin-4-yl)-piperazin-1-yl]acetyl]phenoxyacetate dihydrochloride in the same manner as in Example 8 except that proton sponge and 1-acetoxy-2-methylpropyl-4-nitrophenyl carbonate were used in an amount of 100 mg and 132 mg, respectively.

b) To a solution of 148 mg of the compound obtained in the above step a) in 1 ml of ethanol were added 258 μl of 1N hydrochloric acid and 4 ml of water. The reaction mixture was then concentrated under reduced pressure, lyophilized to give 130 mg of the title compound (82.8%).

¹H-NMR (D₂O) δ: 0.87 (3H, dd, J=1.9 Hz, 6.8 Hz), 1.17 (6H, d, J=6.2 Hz), 1.50–1.75 (2H, m), 1.90–2.20 (6H, m), 2.75–3.00 (2H, m), 3.52–3.73(5H, m), 4.04 (2H, s), 4.08–4.30 (2H, m), 4.77 (2H, s), 4.93 (2H, s), 5.02 (1H, sept, J=6.2 Hz), 7.00 (2H, d, J=9.0 Hz), 7.91 (2H, d, J=9.0 Hz). TSPMS (m/z): 576 (M+H⁺).

Example 20

Cyclohexyl 4-[[4-[1-(1-Acetoxy-2-methylpropyl)oxycarbonylpiperidin-4-yl]-2-oxopiperazin-1-yl]acetyl]phenoxyacetate Hydrochloride a) The title compound was obtained in a yield of 164 mg as a free base from 150 mg of cyclohexyl 4-[[2-oxo-4-(piperidin-4-yl)piperazin-1-yl]-acetyl]phenoxyacetate dihydrochloride in the same manner as in Example 8 except that proton sponge and 1-acetoxy-2-methylpropyl 4-nitrophenyl carbonate were used in an amount of 122 mg and 93 mg, respectively.

b) To a solution of 164 mg of the compound obtained in the above step a) in 2 ml of ethanol were added 259 μl of 1N hydrochloric acid and 8 ml of water. The reaction mixture was then concentrated under reduced pressure, lyophilized to give 164.5 mg (97.4%) of the title compound.

¹H-NMR (D₂O) δ: 0.87 (3H, dd, J=2.2 Hz, 6.9 Hz), 1.13–1.80 (12H, m), 1.93–2.30 (6H, m), 2.75–3.00 (2H, m), 3.55–3.75 (1H, m), 3.68 (4H, s), 4.06 (2H, s), 4.09–4.31 (2H, m), 4.90 (2H, s), 5.05 (2H, s), 6.33–6.42 (1H, m), 7.01 (2H, d, J=9.0 Hz), 7.92 (2H, d, J=9.0 Hz). TSPMS (m/z): 616 (M+H⁺).

Example 21

Ethyl 4-[[4-[1-(1-Acetoxy-2,2-dimethylpropyl)oxycarbonylpiperidin-4-yl]-2-oxopiperazin-1-yl]acetyl]phenoxyacetate The title compound was obtained from 112 mg of ethyl 4-[[2-oxo-4-(piperidin-4-yl)piperazin-1-yl]acetyl]phenoxyacetate dihydrochloride synthesized according to the method described in WO962503 in the same manner as in Example 8 except that N,N-dimethylformamide, proton sponge and 1-acetoxy-2,2-dimethylpropyl 4-nitrophenyl carbonate were used in an amount of 2 ml, 125 mg and 104 mg, respectively.

$^1$H-NMR (CDCl$_3$) δ: 0.97 (9H, s), 1.30 (3H, t, J=7.1 Hz), 1.40–1.55 (2H, m), 1.80–1.90 (2H, m), 2.09 (3H, s), 2.45–2.55 (1H, m), 2.85 (4H, brs), 3.30–3.42 (4H, m), 4.00–4.28 (2H, m), 4.28 (2H, q, J=7.1 Hz), 4.69 (2H, s), 4.77 (2H, s), 6.54 (1H, s), 6.96 (2H, d, J=9.0 Hz), 7.95 (2H, d, J=9.0 Hz).

Example 22

Ethyl 4-[[2-oxo-4-[1-(1-Propionyloxy-2-methylpropyl)oxycarbonylpiperidin-4-yl]piperazin-1-yl]acetyl]phenoxyacetate Hydrochloride a) To a solution of 0.75 g of ethyl 4-[[2-oxo-4-(piperidin-4-yl)-piperazin-1-yl]acetyl]phenoxyacetate dihydrochloride synthesized according to the method described in WO962503 in 16 ml of methylene chloride was added 1.11 g of proton sponge under ice-cooling. After stirring for 5 minutes, the mixture was cooled to −40° C., and a solution of 0.322 g of 1-chloro-2-methylpropyl chloroformate in 2 ml of methylene chloride. After stirring for 45 minutes, the reaction mixture was diluted with ethyl acetate and water, and the organic layer was separated. The aqueous layer was extracted with ethyl acetate. The organic layer collected was washed with saturated aqueous saline, dried over sodium sulfate, and the solvent was removed by distillation. The residue was purified by chromatography on a silica gel column (methylene chloride:methanol=50:1–40:1) to give 0.624 g (74%) of ethyl 4-[[4-[1-(1-chloroethoxycarbonyl)piperidin-4-yl]-2-oxopiperazin-1-yl]acetyl]phenoxyacetate.

$^1$H-NMR (CDCl$_3$) δ: 1.06 (3H, d, J=4.4 Hz), 1.08 (3H, d, J=4.4 Hz), 1.30 (3H, t, J=7.3 Hz), 1.40–1.50 (2H, m), 1.87 (2H, m), 2.19 (1H, m), 2.52 (1H, m), 2.80–3.00 (4H, m), 3.33–3.42 (4H, m), 4.07–4.33 (2H, m), 4.28 (2H, q, J=7.3 Hz), 4.69 (2H, s), 4.78 (2H, s), 6.34 (1H, d, J=4.4 Hz), 6.96 (2H, d, J=9.0 Hz), 7.95 (2H, d, J=9.0 Hz). FABMS (m/z): 538 (M+H$^+$).

b) To a solution of 226 mg of the compound obtained in the above step a) in 2.0 ml of dimethylformamide were added 342 mg of cesium carbonate and a solution of 190 μl in 4.2 ml of dimethylformamide, and the mixture was stirred at room temperature for 17 hours. After stirring at 40° C. for further 10 hours, the mixture was diluted with ethyl acetate and water under ice-cooling, and the organic layer was separated. The aqueous layer was extracted with ethyl acetate. The organic layers combined were washed with saturated aqueous saline, dried over sodium sulfate, and the solvent was removed by distillation. The residue was purified by chromatography on a column (methylene chloride:methanol=50:1) to give 152 mg (63%) of ethyl 4-[[4-[1-(1-propionyloxyethyl)oxycarbonylpiperidin-4-yl]-2-oxopiperazin-1-yl]acetyl]phenoxyacetate.

$^1$H-NMR (CDCl$_3$) δ: 0.97 (2H, d, J=6.8 Hz), 0.98 (2H, d, J=6.8 Hz), 1.15 (3H, t, J=7.3 Hz), 1.30 (3H, t, J=7.1 Hz), 1.40–1.52 (2H, m), 1.85 (2H, brd, J=10 Hz), 2.00–2.09 (1H, m), 2.36 (2H, q, J=7.3 Hz), 2.46–2.55 (1H, m), 2.86 (4H, brs), 3.33–3.42 (4H, m), 4.06–4.26 (2H, m), 4.28 (2H, q, J=7.1 Hz), 4.69 (2H, s), 4.77 (2H, s), 6.61 (1H, d, J=4.9 Hz), 6.95 (2H, d, J=9.0 Hz), 7.95 (2H, d, J=9.0 Hz). TSPMS (m/z): 576 (M+H$^+$).

c) To a solution of 149 mg of the compound obtained in the above step b) in 2.6 ml of ethanol was added 0.28 ml of 1N hydrochloric acid, and the mixture was stirred at room temperature for 1 hour. After evaporating the solvent and filtering insolubles deposited by ethanol, the solvent was removed by distillation. The residue was diluted with ethyl acetate and ether, and the crystalline product precipitated was collected by filtration to give 125 mg (79%) of the title compound.

Example 23

Ethyl 4-[[2-oxo-4-[1-(1-Propionyloxyethyl)oxycarbonylpiperidin-4-yl]piperazin-1-yl]acetyl]phenoxyacetate Hydrochloride a) Ethyl 4-[[4-[1-(1-Chloroethoxycarbonyl)piperidin-4-yl]-2-oxopiperazin-1-yl]acetyl]phenoxyacetate was obtained in a yield of 270 mg (100%) from 252 mg of ethyl 4-[[2-oxo-4-(piperidin-4-yl)piperazin-1-yl]acetyl]phenoxyacetate dihydrochloride synthesized according to the method described in WO962503 in the same manner as in Example 22a) except that 1-chloro-2-methylpropyl chloroformate was replaced by 1-chloroethyl chloroformate.

b) To a solution of 270 mg of the compound obtained in the above step a) in 2.0 ml of dimethylformamide were added 173 mg of cesium carbonate and 190 μl of propionic acid in 3.3 ml of dimethylformamide, and the mixture was stirred at room temperature for 20 hours. The reaction mixture was diluted with ethyl acetate and water under ice-cooling, and the organic layer was separated. The aqueous layer was extracted with ethyl acetate. The organic layers combined were washed with saturated aqueous saline, dried over sodium sulfate, and the solvent was removed by distillation. The residue was purified by chromatography on a silica gel column (methylene chloride:methanol=40:1) to give 174 mg (60%) of ethyl 4-[[4-[1-(1-propionyloxyethoxycarbonyl)piperidin-4-yl]-2-oxopiperazin-1-yl]acetyl]phenoxyacetate.

$^1$H-NMR (CDCl$_3$) δ: 1.14 (3H, t, J=7.6 Hz), 1.30 (3H, t, J=7.3 Hz), 1.40–1.53 (2H, m), 1.49 (3H, d, J=5.6 Hz), 1.85 (2H, brd, J=12 Hz), 2.34 (2H, m), 2.50 (1H, m), 2.86 (4H, brs), 3.34–3.42 (4H, m), 4.16 (2H, brs), 4.28 (2H, q, J=7.3 Hz), 4.69 (2H, s), 4.77 (2H, s), 6.83 (1H, q, J=5.6 Hz), 6.95 (2H, d, J=9.0 Hz), 7.95 (2H, d, J=9.0 Hz). TSPMS (m/z): 548 (M+H$^+$).

c) The title compound was obtained in a yield of 154 mg (86%) from 168 mg of the compound obtained in the above step b) in the same manner as in Example 22c).

Example 24

Ethyl 4-[[4-(1-Isobutyryloxymethoxycarbonylpiperidin-4-yl)-2-oxopiperazin-1-yl]acetyl]phenoxyacetate Hydrochloride a) To a solution of 175 mg of the compound obtained in Example 1a) in 1 ml of N,N-dimethylformamide were added 188 μl of isobutyric acid and 103 mg of cesium carbonate with stirring at room temperature, and the mixture was stirred at 40° C. for 3 hours and then treated in the same manner as in Example 1b) to give the title compound as a free base in a yield of 144.6 mg.

b) The compound obtained in the above step a) (144.6 mg) was treated in the same manner as in Example 2c) with 255 μl of 1N hydrochloric acid to give the title compound in a yield of 146.7 mg (98.8%).

$^1$H-NMR (D$_2$O) δ: 1.20 (6H, d, J=7.2 Hz), 1.33 (6H, d, J=7.2 Hz), 1.70–1.87 (2H, m), 2.20–2.38 (2H, m), 2.71 (1H, sept, J=7.1 Hz), 2.92–3.15 (2H, m), 3.70–3.82 (1H, m), 3.62 (4H, s), 4.18 (2H, s), 4.33 (4H, q, J=7.2 Hz), 4.92 (2H, s), 5.07 (2H, s), 5.80 (2H, s), 7.13 (2H, d, J=9.0 Hz), 8.03 (2H, d, J=9.0 Hz).

Example 25

Cyclohexyl 4-[[4-(1-Isobutyryloxymethoxycarbonylpiperidin-4-yl)-2-oxopiperazin-1-yl]acetyl]phenoxyacetate To a solution of 166 mg of the compound obtained in Example 3a) in 2 ml of N,N-dimethylformamide were added 84 μl of isobutyric acid and 108 mg of cesium carbonate with stirring at room temperature, and the mixture was stirred at 40° C. for 3 hours, and then treated in the same manner as in Example 1b) to give the title compound in a yield of 118 mg (65.2%).

$^1$H-NMR (CDCl$_3$) δ: 1.18 (6H, d, J=6.8 Hz), 1.20–1.95 (14H, m), 2.45–2.66 (2H, m), 2.77–2.95 (4H, m), 3.33–3.42 (4H, m), 4.07–4.30 (2H, m), 4.67 (2H, s), 4.77 (2H, s), 4.85–4.94 (1H, m), 5.77 (2H, s), 6.95 (2H, d, J=8.8 Hz), 7.95 (2H, d, J=8.8 Hz).

Example 26

Isopropyl 4-[[4-(1-Isobutyryloxymethoxycarbonylpiperidin-4-yl)-2-oxopiperazin-1-yl]acetyl]phenoxyacetate Hydrochloride a) Isopropyl 4-[[4-(1-chloromethoxycarbonylpiperidin-4-yl)-2-oxo-piperazin-1-yl]acetyl]phenoxyacetate was obtained as a crude syrup in a yield of 130 mg from 125 mg of 4-[[2-oxo-4-(piperidin-4-yl)piperazin-1-yl]acetyl]phenoxyacetate dihydrochloride in the same manner as in Example 1a).

b) To a solution of 130 mg of the compound obtained in the above step a) in a mixed solvent of 2 ml of N,N-dimethylformamide and 6 ml of tetrahydrofuran were added 145 μl of isobutyric acid and 268 mg of cesium carbonate with stirring at room temperature, and the mixture was stirred at 50° C. for 3 days. The reaction mixture was then poured into 10 ml of water, extracted three times with 20 ml of ethyl acetate, dried over magnesium sulfate, and the solvent was removed by distillation. The residue thus obtained was purified by chromatography on an LH-20 column (chloroform:methanol=1:1) to give the title compound in a yield of 97.9 mg as a free base.

c) To a solution of 97.9 mg of the compound obtained in the above step b) in 1 ml of ethyl acetate were added dropwise 50 μl of 4N hydrochloric acid-ethyl acetate followed by 5 ml of n-hexane. The crystalline product precipitated was collected by filtration to give the title compound in a yield of 97.3 mg (64%) as the hydrochloride salt.

$^1$H-NMR (acetone-d$_6$) δ: 1.13 (6H, d, J=6.9 Hz), 1.23 (6H, d, J=6.1 Hz), 1.83–2.08 (2H, m), 2.28–2.46 (2H, m), 2.58 (1H, sept, J=6.9 Hz), 2.80–3.08 (4H, m), 3.40–3.70 (4H, m), 3.75–3.95 (2H, m), 4.10–4.35 (2H, m), 4.83 (2H, s), 5.06 (1H, sept, J=6.1 Hz), 5.28–5.45 (1H, m), 5.74 (2H, s), 7.06 (2H, d, J=9.0 Hz), 8.03 (2H, d, J=9.0 Hz). TSPMS (m/z): 579 (M+NH$_4^+$).

Example 27

Ethyl 4-[[4-[1-(1-Isobutyryloxyethyl)oxycarbonylpiperidin-4-yl]-2-oxopiperazin-1-yl]acetyl]phenoxyacetate Hydrochloride a) Ethyl 4-[[4-[1-(1-isobutyryloxyethyl)oxycarbonylpiperidin-4-yl]-2-oxopiperazin-1-yl]acetyl]phenoxyacetate was obtained in a yield of 185 mg (62%) from 270 mg of the compound obtained in Example 23a) in the same manner as in Example 23b) except that propionic acid was replaced by isobutyric acid.

$^1$H-NMR (CDCl$_3$) δ: 1.17 (6H, d, J=6.8 Hz), 1.30 (3H, t, J=7.1 Hz), 1.38–1.53 (2H, m), 1.49 (2H, d, J=5.4 Hz), 1.84 (2H, brd, J=11 Hz), 2.46–2.59 (4H, m), 2.85 (2H, brs), 3.33–3.41 (4H, m), 4.05–4.26 (2H, m), 4.28 (2H, q, J=7.1 Hz), 4.69 (2H, s), 4.77 (2H, s), 6.80 (1H, q, J=5.4 Hz), 6.95 (2H, d, J=9.0 Hz), 7.95 (2H, d, J=9.0 Hz). EIMS (m/z): 561 (M$^+$).

b) The title compound was obtained in a yield of 136 mg (71%) from 180 mg of the compound obtained in the above step a) in the same manner as in Example 22c).

Example 28

Ethyl 4-[[4-[1-(1-Isobutyryloxy-2-methylpropyl)oxycarbonylpiperidin-4-yl]-2-oxopiperazin-1-yl]acetyl]phenoxyacetate Hydrochloride a) The title compound was obtained in a yield of 145 mg (59%) as a free base from 226 mg of the compound obtained in Example 22a) in the same manner as in Example 22b) except that propionic acid was replaced by isobutyric acid.

$^1$H-NMR (CDCl$_3$) δ: 0.98 (6H, d, J=6.8 Hz), 1.17 (3H, d, J=7.1 Hz), 1.18 (3H, t, J=7.1 Hz), 1.30 (3H, t, J=7.1 Hz), 1.37–1.60 (2H, m), 1.85 (2H, brd, J=11.0 Hz), 2.05 (1H, m), 2.46–2.61 (4H, m), 2.86 (4H, brs), 3.31–3.41 (4H, m), 4.04–4.32 (2H, m), 4.28 (2H, q, J=7.1 Hz), 4.69 (2H, s), 4.77 (2H, s), 6.59 (1H, d, J=5.1 Hz), 6.96 (2H, d, J=9.0 Hz), 7.95 (2H, d, J=9.0 Hz). EIMS (m/z): 589 (M$^+$).

b) The title compound was obtained in a yield of 122 mg (81%) from 142 mg of the compound obtained in the above step b) in the same manner as in Example 22c).

Example 29

Ethyl 4-[[2-oxo-4-(1-Pivaloyloxymethoxycarbonylpiperidin-4-yl)piperazin-1-yl]acetyl]phenoxyacetate Hydrochloride a) To a solution of 34.1 g of the compound obtained in Example 2a) in 340 ml of N,N-dimethylformamide were added 7.7 g of pivalic acid and 10.5 g of potassium carbonate with stirring at room temperature, and the mixture was stirred at 40° C. for 3 hours and then treated in the same manner as in Example 1b) to give the free base of the title compound.

b) To a solution of the compound obtained in the above step a) in 550 ml of ethyl acetate was added 69 ml of 1N hydrochloric acid-ethanol, and the crystalline product precipitated was collected by filtration and further recrystallized from ethanol:water=5:1 to give the title compound (35 g, 85.4%).

$^1$H-NMR (D$_2$O) δ: 1.20 (9H, s), 1.28 (3H, t, J=7.2 Hz), 1.63–1.83 (2H, m), 2.16–2.32 (2H, m), 2.89–3.08 (2H, m), 3.62–3.80 (1H, m), 3.77 (3H, s), 4.14 (2H, s), 4.29 (2H, q, J=7.2 Hz), 4.00–4.60 (2H, m), 4.90 (2H, s), 5.05 (2H, s), 5.76 (2H, s), 7.11 (2H, d, J=9.0 Hz), 8.02 (2H, d, J=9.0 Hz). TSPMS (m/z): 562 (M+H$^+$).

Example 30

Isopropyl 4-[[2-oxo-4-(1-Pivaloyloxymethoxycarbonylpiperidin-4-yl)piperazin-1-yl]acetyl]phenoxyacetate To a solution of 152 mg of the compound obtained in Example 26a) in a mixed solvent of 2 ml of N,N- dimethylformamide and 6 ml of tetrahydrofuran were added 201 mg of pivalic acid and 252 mg of cesium carbonate with stirring at room temperature, and the mixture was stirred at 50° C. for 3 days. The reaction mixture was poured into 10 ml of water and extracted three times with 20 ml of ethyl acetate. The combined organic layer was dried over magnesium sulfate, and the solvent was removed by distillation. The residue thus obtained was purified by chromatography on an LH-20 column (chloroform:methanol=1:1) to give the title compound (138 mg, 80%).

$^1$H-NMR (CDCl$_3$) δ: 1.22 (9H, s), 1.28 (6H, d, J=6.4 Hz), 1.28–1.55 (2H, m), 1.86 (2H, br), 2.45–2.55 (1H, m), 2.78–2.95 (4H, m), 3.36 (2H, s), 3.38 (2H, t, J=5.6 Hz), 4.05–4.28 (2H, m), 4.66 (2H, s), 4.78 (2H, s), 5.15 (1H, sept, J=6.4 Hz), 5.77 (2H, s), 6.95 (2H, d, J=9.2 Hz), 7.95 (2H, d, J=9.2 Hz). TSPMS (m/z): 593 (M+NH$_4$$^+$).

Example 31

Cyclohexyl 4-[[2-oxo-4-(1-Pivaloyloxymethoxycarbonylpiperidin-4-yl)piperazin-1-yl]acetyl]phenoxyacetate To a solution of 166 mg of the compound obtained in Example 3a) in 1 ml of N,N-dimethylformamide were added 92 mg of pivalic acid and 108 mg of cesium carbonate with stirring at room temperature, and the mixture was stirred at 40° C. for 3 hours and then treated in the same manner as in Example 1b) to give 126.1 mg (68.2%) of the title compound.

$^1$H-NMR (CDCl$_3$) δ: 1.22 (9H, s), 1.20–1.95 (10H, m), 2.45–2.57 (1H, m), 2.78–2.95 (4H, m), 4.10–4.30 (2H, m), 4.78 (2H, s), 4.78 (2H, s), 4.85–4.95 (1H, m), 5.77 (2H, s), 6.94 (2H, d, J=9.0 Hz), 7.93 (2H, d, J=9.0 Hz). TSPMS (m/z): 616 (M+H$^+$).

Example 32

2,2,2-Trichloroethyl 4-[[2-oxo-4-(1-Pivaloyloxymethoxycarbonylpiperidin-4-yl)piperazin-1-yl]acetyl]phenoxyacetate The title compound was obtained in a yield of 0.612 g (50%) from 2,2,2-trichloroethyl 4-[[2-oxo-4-(piperidin-4-yl)piperazin-1-yl]acetyl]phenoxyacetate dihydrochloride (1.01 g) in the same manner as in Example 29.

$^1$H-NMR (CDCl$_3$) δ: 1.22 (9H, s), 1.34–1.55 (2H, m), 1.85 (2H, brs), 2.51 (1H, tt, J=10.8 Hz, 3.6 Hz), 2.80–2.95 (4H, m), 3.36 (2H, s), 3.38 (2H, d, J=5.6 Hz), 4.05–4.28 (2H, m), 4.78 (2H, s), 4.87 (2H, s), 4.88 (2H, s), 5.77 (2H, s), 6.99 (2H, d, J=8.8 Hz), 7.96 (2H, d, J=8.8 Hz). TSPMS (m/z): 666 (M+H$^+$).

Example 33

4-[[2-oxo-4-(1-Pivaloyloxymethoxycarbonylpiperidin-4-yl)piperazin-1-yl]acetyl]phenoxyacetic Acid To a solution of 500 mg of the compound obtained in Example 32 in 10 ml of acetic acid was added 1.05 g of zinc dust with stirring at room temperature, and the mixture was stirred for 3 hours. The suspension of the reaction mixture was filtered through celite, and the filtrate was concentrated under reduced pressure. The residue thus obtained was purified by chromatography on an LH-20 column (methanol:water=1:1) to give the title compound in a yield of 216.3 mg (53.9%).

$^1$H-NMR (CD$_3$OD) δ: 1.19 (9H, s), 1.35–1.52 (2H, m), 1.94 (2H, brs), 2.63–2.73 (1H, s), 2.80–3.03 (4H, m), 3.37–3.47 (4H, m), 4.07–4.23 (1H, m), 4.75 (2H, s), 4.86 (2H, s), 5.74 (2H, s), 7.04 (2H, d, J=9.0 Hz), 7.99 (2H, d, J=9.0 Hz). TSPMS (m/z): 532 (M$^-$).

Example 34

Ethyl 4-[[2-oxo-4-[1-(1-Pivaloyloxyethoxycarbonyl)piperidin-4-yl]piperazin-1-yl]acetyl]phenoxyacetate Hydrochloride a) The free base of the title compound was obtained in a yield of 175 mg (58%) from 265 mg of the compound obtained in Example 5a) in the same manner as in Example 1b) except that acetic acid was replaced by pivalic acid.

$^1$H-NMR (CDCl$_3$) δ: 1.20 (9H, s), 1.30 (3H, t, J=7.2 Hz), 1.38–1.51 (2H, m), 1.48 (3H, d, J=5.4 Hz), 1.84 (2H, brd, J=11.0 Hz); 2.50 (1H, m), 2.85 (4H, brs), 3.34–3.40 (4H, m), 4.05–4.26 (2H, m), 4.28 (2H, q, J=7.1 Hz), 4.69 (2H, s), 4.77 (2H, s), 6.78 (1H, q, J=5.4 Hz), 6.94 (2H, d, J=9.0 Hz), 7.95 (2H, d, J=9.0 Hz). EIMS (m/z): 575 (M$^+$).

b) The title compound was obtained in a yield of 122 mg (67%) from 171 mg of the compound obtained in the above step a) in the same manner as in Example 22c).

Example 35

Ethyl 4-[[2-oxo-4-[1-(1-Pivaloyloxy-2-methylpropyloxycarbonyl)piperidin-4-yl]piperazin-1-yl]acetyl]phenoxyacetate Hydrochloride a) The free base of the title compound was obtained in a yield of 188 mg (71%) from 237 mg of the compound obtained in Example 22a) in the same manner as in Example 1b) except that acetic acid was replaced by pivalic acid.

$^1$H-NMR (CDCl$_3$) δ: 0.98 (6H, d, J=6.8 Hz), 1.21 (9H, s), 1.30 (3H, t, J=7.1 Hz), 1.46 (2H, brs), 1.85 (2H, m), 2.08 (1H, m), 2.51 (1H, m), 2.85 (4H, brs), 3.30–3.42 (4H, m), 4.04–4.32 (2H, m), 4.28 (2H, q, J=7.1 Hz), 4.69 (2H, s), 4.77 (2H, s), 6.56 (1H, d, J=4.9 Hz), 6.95 (2H, d, J=9.0 Hz), 7.95 (2H, d, J=9.0 Hz). FABMS (m/z): 604 (M+H$^+$).

b) The title compound was obtained in a yield of 153 mg (77%) from 183 mg of the compound obtained in the above step a) in the same manner as in Example 22c).

Example 36 n-Butyl 4-[[4-[(5-Methyl-2-oxo-1,3-dioxol-4-yl)methyloxycarbonylpiperidin-4-yl]-2-oxopiperazin-1-yl]acetyl]phenoxyacetate The title compound was obtained in a yield of 89.3 mg (86.7%) from 89 mg of n-butyl 4-[[2-oxo-4-(piperidin-4-yl)piperazin-1-yl]acetyl]phenoxyacetate dihydrochloride synthesized according to the method described in WO962503 in the same manner as in Example 8 except that N,N-dimethylformamide and proton sponge were used in an amount of 0.5 ml and 76 mg, respectively, and 1-acetoxyethyl 4-nitrophenyl carbonate was replaced by 52 mg of (5-methyl-2-oxo-1,3-dioxol-4-yl)methyl 4-nitrophenyl carbonate.

$^1$H-NMR (CDCl$_3$) δ: 0.93 (3H, t, J=7.4 Hz), 1.29–1.71 (6H, m), 1.77–1.94 (2H, m), 2.19 (3H, s), 2.42–2.57 (1H, m), 2.78–2.96 (4H, m), 3.32–3.42 (4H, m), 4.00–4.25 (2H, m), 4.21 (2H, t, J=6.7 Hz), 4.69 (2H, s), 4.77 (2H, s), 4.79–4.92 (2H, m), 6.81 (1H, q, J=5.5 Hz), 6.95 (2H, d, J=9.0 Hz), 7.95 (2H, d, J=9.0 Hz). EIMS (m/z): 587 (M$^+$).

Example 37

1-Methylpentyl 4-[[4-[(5-Methyl-2-oxo-1,3-dioxol-4-yl)methyloxycarbonylpiperidin-4-yl]-2-oxopiperazin-1-yl]acetyl]phenoxyacetate The title compound was obtained in a yield of 166 mg (95.3%) from 150 mg of 1-methylpentyl 4-[[2-oxo-4-(piperidin-4-yl)piperazin-1-yl]acetyl]phenoxyacetate dihydrochloride synthesized according to the method described in WO962503 in the same manner as in Example 8 except that N,N-dimethylformamide and proton sponge were used in an amount of 1 ml and 127 mg, respectively, and 1-acetoxyethyl 4-nitro-phenyl carbonate was replaced by 84 mg of (5-methyl-2-oxo-1,3-dioxol-4-yl)methyl 4-nitrophenyl carbonate.

$^1$H-NMR (CDCl$_3$) δ: 0.83 (3H, t, J=7.1 Hz), 1.16–1.35 (8H, m), 1.40–1.65 (3H, m), 1.75–1.95 (2H, m), 2.16 (3H, s), 2.40–2.60 (1H, m), 2.75–2.95 (4H, m), 3.30–3.40 (4H, m), 4.00–4.25 (2H, m), 4.64 (2H, s), 4.74 (2H, s), 4.77–4.87 (2H, m), 4.95–5.07 (1H, m), 6.92 (1H, d, J=9.0 Hz), 7.91 (2H, d, J=9.0 Hz). TSPMS (m/z): 616 (M+H$^+$).

Example 38

Cyclohexyl 4-[[4-[(5-Methyl-2-oxo-1,3-dioxol-4-yl)methyloxycarbonylpiperidin-4-yl]-2-oxopiperazin-1-yl]acetyl]phenoxyacetate The title compound was obtained in a yield of 162.8 mg (93.2%) from 150 mg of cyclohexyl 4-[[2-oxo-4-(piperidin-4-yl)piperazin-1-yl]acetyl]phenoxyacetate dihydrochloride synthesized according to the method described in WO962503 in the same manner as in Example 8 except that N,N-dimethyformamide and proton sponge were used in an amount of 1 ml and 127 mg, respectively, and 1-acetoxyethyl 4-nitrophenyl carbonate was replaced by 84 mg of (5-methyl-2-oxo-1,3-dioxol-4-yl)methyl 4-nitrophenyl carbonate.

$^1$H-NMR (CDCl$_3$) δ: 1.21–1.75 (8H, m), 1.80–1.94 (4H, m), 2.18 (3H, s), 2.55–2.57 (1H, m), 2.77–2.97 (4H, m), 3.35–3.42 (4H, m), 3.48 (2H, s), 3.93–4.25 (2H, m), 4.66 (2H, s), 4.77 (2H, s), 4.77–4.96 (3H, m), 6.94 (1H, d, J=9.0 Hz), 7.74 (2H, d, J=9.0 Hz). TSPMS (m/z): 614 (M+H$^+$).

Example 39

Ethyl 4-[[2-oxo-4-[(Z)-2-(3-Phthalidyliden)ethyloxycarbonylpiperidin-4-yl]piperazin-1-yl]acetyl]phenoxyacetate The title compound was obtained in a yield of 114.4 mg (92.3%) from 70 mg of ethyl 4-[[2-oxo-4-(piperidin-4-yl)piperazin-1-yl]acetyl]phenoxyacetate dihydrochloride synthesized according to the method described in WO962503 in the same manner as in Example 8 except that N,N-dimethyformamide and proton sponge were used in an amount of 1 ml and 88 mg, respectively, and 1-acetoxyethyl-4-nitrophenyl carbonate was replaced 70 mg of (Z)-2-(3-phthalidyliden)ethyl 4-nitrophenyl carbonate.

$^1$H-NMR (CDCl$_3$) δ: 1.28 (3H, t, J=7.2 Hz), 1.35–1.54 (2H, m), 1.75–1.90 (2H, m), 2.42–2.55 (1H, m), 2.75–2.93 (4H, m), 3.30–3.42 (4H, m), 4.00–4.30 (2H, s), 4.26 (2H, q, J=7.2 Hz), 4.67 (2H, s), 4.75 (2H, s), 4.99 (2H, d, J=7.0 Hz), 5.80 (1H, t, J=7.0 Hz), 6.92 (2H, d, J=9.0 Hz), 7.57–7.60 (1H, m), 7.65–7.74 (2H, m), 7.88–7.97 (3H, m). TSPMS (m/z): 606 (M+H$^+$).

Example 40

Cyclohexyl 4-[[2-oxo-4-[(Z)-2-(3-Phthalidyliden)ethyloxycarbonylpiperidin-4-yl]piperazin-1-yl]acetyl]phenoxyacetate The title compound was obtained in a yield of 130.2 mg (96.2%) from 109 mg of cyclohexyl 4-[[2-oxo-4-(piperidin-4-yl)piperazin-1-yl]acetyl]phenoxyacetate dihydrochloride synthesized according to the method described in WO962503 in the same manner as in Example 8 except that N,N-dimethyformamide and proton sponge were used in an amount of 1 ml and 88 mg, respectively, and 1-acetoxyethyl 4-nitrophenyl carbonate was replaced by 70 mg of (Z)-2-(3-phthalidyliden)ethyl 4-nitrophenyl carbonate.

$^1$H-NMR (CDCl$_3$) δ: 1.20–1.74 (10H, m), 1.78–1.90 (4H, m), 2.42–2.55 (1H, m), 2.76–2.91 (4H, m), 3.30–3.40 (4H, m), 4.18 (2H, brs), 4.65 (2H, s), 4.75 (2H, s), 4.83–4.92 (1H, m), 4.99 (2H, d, J=7.0 Hz), 5.80 (1H, t, J=7.0 Hz), 6.91 (2H, d, J=9.0 Hz), 7.53–7.59 (1H, m), 7.65–7.74 (2H, m), 7.87–7.95 (3H, m). TSPMS (m/z): 660 (M+H$^+$).

Example 41

Ethyl 4-[[2-oxo-4-(1-Pivaloyloxymethoxycarbonylpiperidin-4-yl)piperazin-1-yl]acetyl]phenoxyacetate(the same compound as that in Example 29)

a) To a solution 42.5 g of 2-oxopiperazine synthesized according to the method described in J. Am. Chem. Soc., 62, 1202 (1940) in 500 ml of N,N-dimethylformamide were added 59.2 ml of trimethylamine and 97.5 ml of di-t-butyl dicarbonate dropwise in this sequence at room temperature, and the mixture was stirred at room temperature for 20 hours. The reaction mixture was diluted with 50 ml of water and stirred at room temperature for 10 minutes, and N,N-dimethylformamide and water were removed by distillation under reduced pressure. The residue thus obtained was washed with diethyl ether to give 39.7 g (47%) of 1-t-butyloxycarbonyl-3-oxopiperazine.

$^1$H-NMR (CDCl$_3$) δ: 1.44 (9H, s), 3.36–3.42 (2H, m), 3.64 (2H, t, J=5.1 Hz), {4.85, 6.32, (1H, brs)}.

b) To 80 ml of formic acid was added 28 ml of acetic anhydride at room temperature, and the mixture was stirred at 60° C. for 20 minutes. After stirring at room temperature for further 15 minutes, the reaction mixture was added dropwise to a solution of 4.2 g of 2-oxopiperazine in 400 ml of methylene chloride at 0° C. over a period of 1.25 hours, and the resulting mixture was stirred at 0° C. for further 30 minutes. The solvent was removed by distillation under reduced pressure, and the residue thus obtained was recrystallized from acetone/hexane to give 3.0 g (56%) of 1-formyl-3-oxopiperazine.

$^1$H-NMR (CDCl$_3$) δ: {3.42, 3.47 (2H, dt, J=5.6 Hz, 2.7 Hz)}, {3.64, 3.80 (2H, t, J=5.6 Hz)}, {4.07, 4.21 (2H, s)}, {6.24, 6.41 (1H, brs)}, {8.12, 8.14 (1H, s)}.

c) To a suspension of 1.4 g of sodium hydride in 130 ml of tetrahydrofuran was added 6.2 g of the compound obtained in the paragraph (a) at room temperature, and the mixture was stirred at room temperature for 25 minutes. After cooling it to 0° C., a solution of 4.7 g of ethyl 4-(bromoacetyl)phenoxyacetate in 120 ml of tetrahydrofuran was added dropwise over a period of 45 minutes, and the resulting mixture was further stirred at 0° C. for 20 minutes. The reaction was terminated with 100 ml of a saturated aqueous ammonium chloride solution, and the mixture was extracted three times with 100 ml of ethyl acetate. The organic layer collected was washed with 100 ml of saturated aqueous saline, and dried over anhydrous sodium sulfate. After the solvent was removed by distillation under reduced pressure, the residue thus obtained was purified by chromatography on a silica gel column (methylene chloride/acetone=4/1) to give 6.5 g (99%) of ethyl 4-((1-t-butyloxycarbonyl-3-oxopiperazin-4-yl)acetyl)phenoxyacetate.

¹H-NMR (CDCl₃) δ: 1.31 (3H, t, J=7.1 Hz), 1.44 (9H, s), 3.43 (2H, t, J=5.4 Hz), 3.75 (2H, t, J=5.4 Hz), 4.18 (2H, s), 4.28 (2H, q, J=7.1 Hz), 4.70 (2H, s), 4.83 (2H, s), 6.97 (2H, d, J=9.0 Hz), 7.95 (2H, d, J=9.0 Hz).

d) To a suspension of 22 mg of sodium hydride in 3 ml of N,N-dimethylformamide was added 64 mg of the compound obtained in (b) at 22° C. The mixture was stirred at 22° C. for additional 25 minutes. To this reaction mixture was added dropwise a solution of 168 mg of ethyl 4-(bromoacetyl)phenoxyacetate in 5 ml of tetrahydrofuran at 22° C. over a period of 5 minutes, and the resulting mixture was stirred at 22° C. for additional 5 minutes. The reaction was terminated with 10 ml of a saturated aqueous ammonium chloride solution, and the mixture was extracted five times with 10 ml of ethyl acetate. The organic layer collected was dried over anhydrous sodium sulfate, and the solvent was removed by distillation under reduced pressure. The residue thus obtained was purified by chromatography on a silica gel column (methylene chloride/methanol=95/5) to give 104 mg (60%) of ethyl 4-((1-formyl-3-oxopiperazin-4-yl)acetyl)phenoxyacetate.

¹H-NMR (CDCl₃) δ: 1.30 (3H, t, J=7.1 Hz), {3.43, 3.48 (2H, t, J=5.4 Hz)}, {3.74, 3.86 (2H, t, J=5.4 Hz)}, {4.14, 4.24 (2H, s)}, 4.27 (2H, q, J=7.1 Hz), 4.70 (2H, s), {4.81, 4.83 (2H, s)}, 6.96 (2H, d, J=8.8 Hz)}, 7.93 (2H, d, J=8.8 Hz)}, {8.11, 8.12 (1H, s)}.

e) To a solution of 7.2 g of the compound obtained in (c) in 10 ml of ethyl acetate was added 35 ml of 4N-hydrochloric acid/ethyl acetate, and the mixture was stirred at room temperature for 24 hours, and filtered through a glass filter. The salt obtained was dried under reduced pressure to give 5.0 g (82%) of ethyl 4-((2-oxopiperazin-1-yl)acetyl)phenoxyacetate hydrochloride.

¹H-NMR (CD₃OD) δ: 1.28 (3H, t, J=7.0 Hz), 3.59–3.64 (2H, m), 3.67–3.72 (2H, m), 3.95 (2H, s), 4.25 (2H, q, J=7.0 Hz), 4.82 (2H, s), 4.98 (2H, s), 7.06 (2H, d, J=8.9 Hz), 8.01 (2H, d, J=8.9 Hz).

f) To a solution of 52 mg of the compound obtained in (d) in 2 ml of a mixed solvent of ethyl acetate/ethanol=1/1 was added 2 ml of 4N-hydrochloric acid/ethyl acetate, and the mixture was stirred at room temperature for 12 hours. The solvent was removed by distillation under reduced pressure to give 47 mg (88%) of ethyl 4-((2-oxopiperazin-1-yl)acetyl)phenoxyacetate hydrochloride.

g) To a solution of 1 g of 4-oxopiperidine hydrochloride monohydrate in 0.7 ml of water was added 2.2 ml of diethyl ether, and the mixture was stirred at 0° C. Chloromethyl chloroformate (0.3 ml) was added dropwise, and the mixture was stirred at 0° C. for 5 minutes. Next, 0.8 ml of a 17N aqueous sodium hydroxide solution and 0.3 ml of chloromethyl chloroformate were divided into three portions and alternately added dropwise, and the resulting mixture was stirred at 0° C. for additional 20 minutes. The reaction mixture was diluted with 5 ml of a saturated aqueous saline, and extracted three times with 5 ml of diethyl ether. The organic layer thus obtained was dried over anhydrous sodium sulfate, and the solvent was removed by distillation under reduced pressure to give 1.7 g (100%) of 1-chloromethoxycarbonyl-4-oxopiperidine.

¹H-NMR (CDCl₃) δ: 2.45–2.56 (4H, m), 3.78–3.87 (4H, m), 5.83 (2H, s).

h) To a suspension of 1.1 g of potassium carbonate in 6 ml of N,N-dimethylformamide was added 822 mg of pivalic acid, and the mixture was stirred at 35° C. for 30 minutes. After dropwise addition of a solution of 1.2 g of the compound obtained in (g) in 12 ml of N,N-dimethylformamide, the mixture was further stirred at 35° C. for 1.5 hours. The reaction mixture was poured into a mixture of 20 ml of a saturated aqueous saline and 20 ml of ethyl acetate, and extracted three times with 20 ml of ethyl acetate. The organic layer thus obtained was dried over anhydrous sodium sulfate, and the solvent was removed by distillation under reduced pressure to give 1.1 g (67%) of 1-pivaloyloxymethoxycarbonyl-4-oxopiperidine.

¹H-NMR (CDCl₃) δ: 1.23 (9H, s), 2.41–2.56 (4H, m), 3.74–3.86 (4H, m), 5.82 (2H, s).

i) To a suspension of 15 mg of sodium borohydride in 1 ml of tetrahydrofuran were added 0.35 ml of acetic acid and 0.1 ml of triethylamine in this sequence at room temperature, and the mixture was stirred for 5 minutes. Then, 3 ml of ethyl acetate, 70 mg of the compound obtained in (e) or (f), and a solution of 104 mg of the compound obtained in (h) in 3 ml of ethyl acetate were added in this sequence. After stirring at room temperature for 3 hours, 1 ml of triethylamine and 10 ml of water were added to stop the reaction, and the mixture was extracted three times with 15 ml. of ethyl acetate. The organic layer thus obtained was dried over anhydrous sodium sulfate, and the solvent was removed by distillation under reduced pressure. The residue was purified by recrystallization from ethanol to give 73 mg (66%) of the title compound.

¹H-NMR (CDCl₃) δ: 1.22 (9H, s), 1.30 (3H, t, J=7.0 Hz), 1.35–1.45 (2H, m), 1.80–1.90 (2H, m), 2.45–2.55 (1H, m), 2.80–2.90 (4H, m), 3.36 (2H, s), 3.38 (2H, t, J=5.4 Hz), 4.10–4.25 (2H, m), 4.28 (2H, q, J=7.0 Hz), 4.69 (2H, s), 4.78 (2H, s), 5.77 (2H, s), 6.96 (2H, d, J=9.0 Hz), 7.95 (2H, d, J=9.0 Hz).

The compounds of the examples have the structure shown in the following table.

| Example | W | R |
|---|---|---|
| 1. | CH₃COOCH₂ | —C₂H₅ |
| 2. | CH₃COOCH₂ | —CH(CH₃)₂ |
| 3. | CH₃COOCH₂ | —⌬ (cyclohexyl) |
| 4. | CH₃COOCH₂ | —CH₂CCl₃ |
| 5. | CH₃COOCH₂ | —H |
| 6. | CH₃COOCH(CH₃) | —CH₂CH₂CH₂CH₃ |
| 7. | CH₃COOCH(CH₃) | —CH₂—⌬ (phenyl) |
| 8. | CH₃COOCH(CH₃) | —C₂H₅ |
| 9. | CH₃COOCH(CH₃) | —⌬ (cyclohexyl) |
| 10. | CH₃COOCH(CH₃) | —CH(CH₃)(CH₂)₃CH₃ |

-continued

| Example | W | R |
|---|---|---|
| 11. | CH₃COOCH(CH₃) | —CH(CH₃)₂ |
| 12. | CH₃COOCH(CH₃) | —CH₃ |
| 13. | CH₃COOCH(CH₃) | tetrahydropyran-4-yl |
| 14. | CH₃COOCH(CH₃) | —CH(CH₂OC₂H₅)₂ |
| 15. | CH₃COOCH(CH₃) | —CH₂CON(CH₃)₂ |
| 16. | CH₃COOCH(C₂H₅) | —C₂H₅ |
| 17. | CH₃COOCH(CH(CH₃)₂) | —C₂H₅ |
| 18. | CH₃COOCH(CH(CH₃)₂) | tetrahydropyran-4-yl |
| 19. | CH₃COOCH(CH(CH₃)₂) | —CH(CH₃)₂ |
| 20. | CH₃COOCH(CH(CH₃)₂) | cyclohexyl |
| 21. | CH₃COOCH(C(CH₃)₃) | —C₂H₅ |
| 22. | C₂H₅COOCH(CH(CH₃)₂) | —C₂H₅ |
| 23. | C₂H₅COOCH(CH₃) | —C₂H₅ |
| 24. | (CH₃)₂CHCOOCH₂ | —C₂H₅ |
| 25. | (CH₃)₂CHCOOCH₂ | cyclohexyl |
| 26. | (CH₃)₂CHCOOCH₂ | —CH(CH₃)₂ |
| 27. | (CH₃)₂CHCOOCH(CH₃) | —C₂H₅ |
| 28. | (CH₃)₂CHCOOCH(CH(CH₃)₂) | —C₂H₅ |
| 29. | (CH₃)₃CCOOCH₂ | —C₂H₅ |
| 30. | (CH₃)₃CCOOCH₂ | —CH(CH₃)₂ |
| 31. | (CH₃)₃CCOOCH₂ | cyclohexyl |
| 32. | (CH₃)₃CCOOCH₂ | —CH₂CCl₃ |
| 33. | (CH₃)₃CCOOCH₂ | —H |
| 34. | (CH₃)₃CCOOCH(CH₃) | —C₂H₅ |
| 35. | (CH₃)₃CCOOCH(CH(CH₃)₂) | —C₂H₅ |
| 36. | 4-methyl-5-methylene-1,3-dioxol-2-one | —CH₂CH₂CH₂CH₃ |
| 37. | 4-methyl-5-methylene-1,3-dioxol-2-one | —CH(CH₃)(CH₂)₃CH₃ |
| 38. | 4-methyl-5-methylene-1,3-dioxol-2-one | cyclohexyl |
| 39. | 3-propylidenephthalid-1-yl | —C₂H₅ |
| 40. | 3-propylidenephthalid-1-yl | cyclohexyl |
| 41. | (CH₃)₃CCOOCH₂ | —C₂H₅ |

Test Example 1

Oral Administration Test

1) Preparation of a Solution to be Administered

The compound was dissolved or suspended in either of the solvents in which the compound is preferably dispersed or dissolved including distilled water, CMC-Na, Tween 80, and HCO 60 to prepare the liquids for intravenous injection and oral administration. The liquids for intravenous injection and oral administration have a concentration of 0.3 mg/ml and 5 mg/ml, respectively. The concentrations of the compounds were determined by HPLC.

2) Bioavailability

Rats having fasted for 16–20 hours were subjected to cannulation with a polyethylene tube (PE50) into femoral artery. The liquid for intravenous injection was administered in a dose of 1 ml to tail vein, and the liquid for oral administration was administered by force in a dose of 2 ml/kg to stomach with an oral sound. After administration, about 300 μl of bloods were collected into microtubes coated with sodium heparin with a passage of period. Sampling times were set at 0.033, 0.083, 0.167, 0.5, 1 and 2 hours in intravenous injection, and 0.25, 0.5, 1, 2, 4 and 6 hours in oral administration. The blood samples were centrifuged at 4° C. at 1,500×g for 20 minutes to give plasma samples. The plasma samples were treated according to the method described below, and the activity substance was then measured by HPLC.

Preliminary Treatment of Plasma

To 50 μl of rat plasma was added 50 μl of 5 μg/ml of internal standard, followed by 0.1% phosphoric acid containing 15 mmole/l of sodium octanesulfonate and distilled water in an amount of 50 μl, respectively. After addition, 400 μl of acetone was added for deproteinization, and the supernatant was collected by cetrifugation at 4° C. for 10 minutes. The supernatant was concentrated under nitrogen gas stream at 40° C. Then, 0.1% phosphoric acid containing 15 mmole/l sodium octanesulfonate was added, and the mixture was mixed sufficiently. After mixing, the mixture was centrifuged again at 1,500 g at 4° C. for 10 minutes, and the supernatant was taken out as a sample for HPLC.

HPLC Condition

Column: YMC-Pack Ph (5 μm), 4.6×250 mm (YMC Co., Ltd.),

Solvent: A; 0.1% $H_3PO_4$+15 mmole/l sodium 1-octanesulfonate, B; acetonitrile, Flow rate: 1.0 ml/min., Detector: UV-280 nm.

3) Pharmacokinetics

Among the observed values after administration, the observed values corresponding to the maximum plasma concentration ($C_{max}$) and the time for reaching the maximum plasma concentration ($T_{max}$) were confirmed. After reaching the $C_{max}$, the gradient (kel) of the eliminating phase was obtained from the three points of the final observed values to calculate the half life ($T_{1/2}$) from 0.693/kel. The area below the plasma concentration-time curve from 0 to infinity (AUCinfinite) was calculated by the trapezoidal method until the final observed value, and after the final observed value from the final observed value/kel as the sum of respective values. In addition, as the dose was used the observed value.

Bioavailability (B.A. (%)) was calculated from the following equation:

B.A. (%)=[(AUC p.o./dose on p.o.)/(AUC i.v./dose on i.v.)]×100

The results are listed below.

| Compounds | B.A. (%) |
|---|---|
| Example 1 | 36.9 |
| Example 29 | 35.4 |
| Example 30 | 35.4 |
| Compound A | 5.0 |
| Compound B | 3.0 |
| Compound C | 0.9 |

Compound A: an active substance compound of the compounds represented by the formula (I); the specific structure is represented as follows:

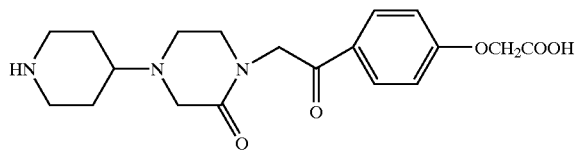

Compound B: Preparation 1

Compound C: [[4-[[[(4,5,6,7-tetrahydrothieno[3,2-c]pyridin-2-yl) carbonyl]amino]acetyl]-o-phenylene]dioxy] diacetic acid as the active substance compound in Preparation 1.

Test Example 2

Platelet Aggregation Inhibiting Effect

Among the compounds represented by the general formula (I) according to the present invention, the platelet aggregation inhibiting effect of the above compound A was examined with human PRP (platelet rich plasma).

A 9 volume sample of blood was taken out through an injection syringe having 1 volume of 3.8% sodium citrate added thereto from the vein of normal human (male), centrifuged at 170×g for 10 minutes at room temperature, and the resulting supernatant was isolated as PRP. The residual blood from which PRP had been isolated was centrifuged at 2,700×g for 15 minutes, and the resulting supernatant was isolated as platelet poor plasma (PPP).

The platelet aggregation test was carried out with AGGRIGOMETER (PAM-8C) manufactured by MEBANICS. The substance to be tested is dissolved in 50% DMSO-physiological saline, 50% methanol-physiological saline, or a physiological saline. The preincubation time of the substance to be tested and PRP was set as 2 minutes. An aggregation driving agent ADP (CHRONO-PARREAGENTS384 ADP, CHRONO-LOG Corp.) was diluted with physiological saline so that the final concentration is 5 μM.

The platelet aggregation inhibiting activity was calculated from the following equation as the suppressive rate against the platelet aggregation inhibiting effect by ADP when no compound to be tested was added:

Platelet aggregation inhibiting activity (%)=

$$\left[1 - \frac{\text{ADP aggregation rate with substance to be tested}}{\text{ADP aggregation rate without substance to be tested}}\right] \times 100$$

The $IC_{50}$ of the general formula (XVIII) calculated from the aggregation rate was 0.042 μM.

What is claimed is:

1. A compound of formula (I):

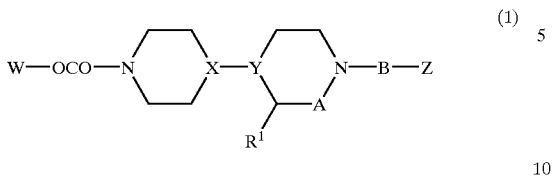

wherein

A represents $CH_2$ or CO,

B represents a group —$(CH_2)_k$—, wherein k is an integer of 1–4, or —$(CH_2)_m$—CO—, wherein m is an integer of 0–3, X and Y are different from each other and represent N or CH, W represents a group represented by formula (a):

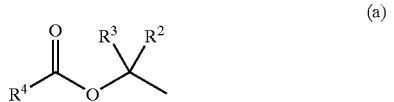

wherein $R^2$ and $R^3$ represent independently a hydrogen atom or $C_{1-6}$ alkyl, $R^4$ represents $C_{1-10}$ alkyl, $C_{2-10}$ alkenyl, $C_{2-5}$ alkynyl, aryl, or $C_{3-8}$ cycloalkyl, or a group represented by formula (b):

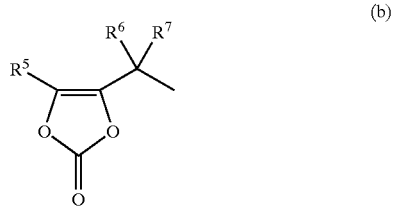

wherein $R^5$ represents a hydrogen atom, $C_{1-6}$ alkyl or $C_{6-8}$ aralkyl, and $R^6$ and $R^7$ independently represent a hydrogen atom or $C_{1-6}$, alkyl, or a group represented by formula (c):

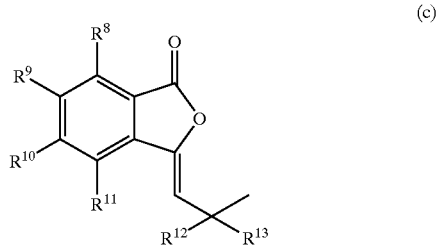

wherein $R^8$, $R^9$, $R^{10}$ and $R^{11}$ independently represent a hydrogen atom, $C_{1-6}$ alkyl or $C_{6-8}$ aralkyl, $R^{12}$ and $R^{13}$ independently represent a hydrogen atom or $C_{1-6}$ alkyl, Z represents a group (II) or (III):

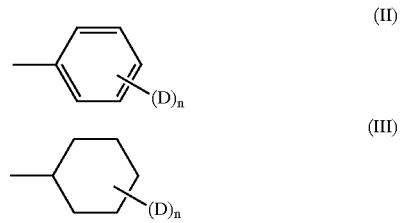

wherein n is an integer of 1–3,

D represents a group —V—$(CH_2)_p$—COOR, wherein V represents —O— or a bond, p is an integer of 1–4, R represents a hydrogen atom, $C_{1-8}$ alkyl which may be substituted by a halogen atom, $C_{5-8}$ cycloalkyl, benzyl, a five- to eight-membered saturated cycloalkyl group containing an oxygen or sulfur atom, 1,3-bis($C_{1-6}$alkoxy)propan-2-yl, 1,3-bis($C_{1-6}$alkylthio)propan-2-yl, $C_{1-6}$alkyl-$(OCH_2CH_2)_q$— wherein q is an integer of 1–3, $C_{1-6}$alkyl-$(SCH_2 CH_2)_r$— wherein r is an integer of 1–3, R'R"NCO—$(CH_2)_s$— wherein s is an integer of 1–3, and R' and R" independently represent a hydrogen atom or $C_{1-6}$ alkyl, or an ester moiety which may be removed under physiological conditions, $R^1$ represents a hydrogen atom or $C_{1-6}$ alkyl which may be substituted by carboxyl, lower alkoxy, carbamoyl, or phenyl, or a pharmaceutically acceptable salt or solvate thereof.

2. A compound according to claim 1, wherein W represents the group (a) where $R^2$ represents a hydrogen atom, $R^3$ represents a hydrogen atom or $C_{1-6}$ alkyl, and $R^4$ represents $C_{1-6}$ alkyl.

3. A compound according to claim 1, wherein W represents the group (b) where $R^5$ represents $C_{1-6}$alkyl, and $R^6$ and $R^7$ represent a hydrogen atom.

4. A compound according to claim 1, wherein W represents the group (c) where $R^8$, $R^9$, $R^{10}$ and $R^{11}$ represent a hydrogen atom, and $R^{12}$ and $R^{13}$ represent a hydrogen atom.

5. A compound according to claim 1, wherein Z represents the group (II) where R represents $C_{1-8}$ alkyl which may be substituted by halogen atoms, $C_{5-8}$ cycloalkyl, benzyl, a five- to eight-membered saturated cycloalkyl group comprising an oxygen or sulfur atom, 1,3-bis($C_{1-6}$alkoxy)propan-2-yl, or a group R'R"NCO—$(CH_2)_s$— where s is 1, and R' and R" independently represent a hydrogen atom or $C_{1-6}$ alkyl.

6. A compound according to claim 5, wherein W represents the group (a) where $R^2$ represents a hydrogen atom or $C_{1-6}$ alkyl, and $R^4$ represents $C_{1-6}$ alkyl.

7. A compound according to claim 5, wherein W represents the group (b) where $R^5$ represents $C_{1-6}$ alkyl, and $R^6$ and $R^7$ represents a hydrogen atom.

8. A compound according to claim 5, wherein W represents the group (c) where $R^8$, $R^9$, $R^{10}$ and $R^{11}$ represent a hydrogen atom, and $R^{12}$ and $R^{13}$ represent a hydrogen atom.

9. A compound according to claim 1, wherein A represents CO, $R^1$ represents a hydrogen atom, X represents CH, and Y represents N.

10. A compound according to claim 9, wherein B represents —$(CH_2)_m$—CO—.

11. A compound according to claim 1, wherein the compound is ethyl 4-[[2-oxo-4-(1-pivaloyloxymethoxycarbonylpiperidin-4-yl)piperazin-1-yl]acetyl]phenoxyacetate, isopropyl 4-[[2-oxo-4-(1-pivaloyloxymethoxycarbonylpiperidin-4-yl)piperazin-1-yl]acetyl]phenoxyacetate, or ethyl 4-[[4-(1-acetoxymethoxycarbonylpiperidin-4-yl)-2-oxopiperazin-1-yl]acetyl]phenoxyacetate.

12. A pharmaceutical composition comprising an effective amount of the compound according to claim 1 or a pharmacologically acceptable salt or solvate thereof together with a pharmacologically acceptable carrier.

13. A pharmaceutical composition according to claim 12, which is used as a platelet aggregation inhibiting agent.

14. A pharmaceutical composition according to claim 12, which is used for the treatment or prophylaxis of a thrombotic disease.

15. A pharmaceutical composition according to claim 14, wherein the thrombotic diseases are cerebral infarction, cardiac infarction, angina pectoris, or peripheral arterial occlusion.

16. A process for preparing a pharmaceutical composition according to claim 12, which comprises mixing an effective amount of the compound according to claim 1 or a pharmacologically acceptable salt or solvate thereof together with a pharmacologically acceptable carrier.

17. A process for treatment or prophylaxis of a thrombotic disease, comprising administering an effective amount of the compound according to claim 1 or a pharmacologically acceptable salt or solvate thereof to a patient in need thereof.

18. A process for preparing the compound of formula (I) defined in claim 1, wherein X is CH, Y is N, and W is a group represented by formula (a):

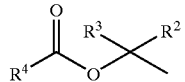

(a)

wherein $R^2$ and $R^3$ represent independently a hydrogen atom or $C_{1-6}$alkyl, and $R^4$ represents $C_{1-10}$ alkyl, $C_{2-10}$ alkenyl, $C_{2-5}$ alkynyl, aryl, or $C_{3-8}$ cycloalkyl, comprising the steps of reacting a compound of formula (IV):

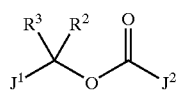

(IV)

wherein $R^2$ and $R^3$ represent independently a hydrogen atom or $C_{1-6}$ alkyl, $R^4$ represents $C_{1-10}$ alkyl, $C_{2-10}$ alkenyl, $C_{2-5}$ alkynyl, aryl or $C_{3-8}$ cycloalkyl, $J^1$ represents a halogen atom or a group which can be easily substituted nucleophilically, and $J^2$ represents a halogen atom or a substituted phenoxy group, with a compound of formula (XVIII):

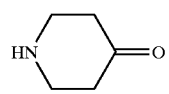

(XVIII)

to obtain a compound of formula (XIX):

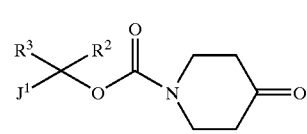

(XIX)

wherein $R^2$, $R^3$ and $J^1$ have the same meanings as defined above, reacting the compound of formula (XIX) with a compound of the formula (VII):

$$R^4COO^-M^+ \quad \text{(VII)}$$

wherein $R^4$ represents $C_{1-10}$ alkyl, $C_{2-10}$ alkenyl, $C_{2-5}$ alkynyl, aryl or $C_{3-8}$ cycloalkyl, and $M^+$ represents a metal ion, to obtain a compound of formula (XVI):

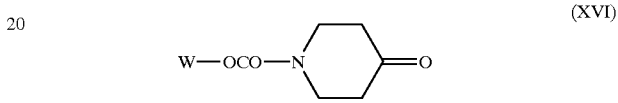

(XVI)

wherein W is a group represented by formula (a):

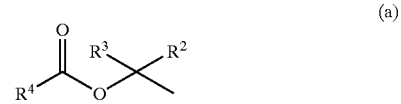

(a)

wherein $R^2$, $R^3$ and $R^4$ have the same meanings as defined above, and reacting the compound of formula (XVI) with a compound of formula (XVII):

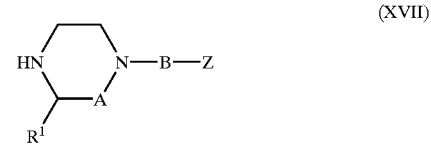

(XVII)

wherein A, B, Z and $R^1$ have the same meanings as defined in formula (I), to obtain the compound of formula (I).

19. A method for preparing the compound of formula (I) according to claim 1,

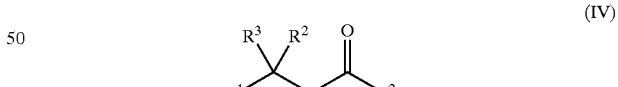

(IV)

in which $R^2$ and $R^3$ represent independently a hydrogen atom or $C_{1-6}$ alkyl, $J^1$ represents a halogen atom or a group which can be easily substituted nucleophilically, and $J^2$ represents a halogen atom or a substituted phenoxy group, with a compound represented by the formula (V):

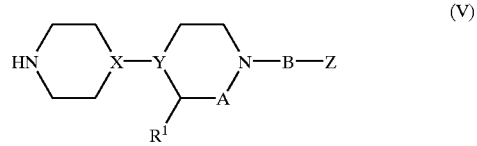

(V)

wherein X, Y, A, B, Z and R¹ have the same meanings as defined in claim 1, to obtain a compound represented by formula (VI):

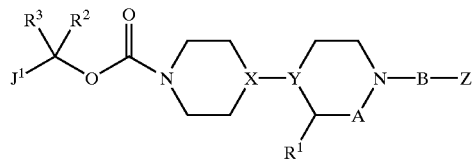

(VI)

wherein R², R³, J¹, X, Y, A, B, Z and R¹ have the same meanings as defined above, and reacting the compound represented by formula (VI) with a compound represented by formula (VII):

R⁴COO⁻M⁺ (VII)

wherein $R^4$ represents $C_{1-10}$ alkyl, $C_{2-10}$ alkenyl, $C_{2-5}$ alkynyl, aryl or $C_{3-8}$ cycloalkyl, and $M^+$ represents a metal ion, to obtain the compound of formula (I) according to claim 1.

* * * * *